United States Patent
Lister-James et al.

(10) Patent No.: US 6,248,304 B1
(45) Date of Patent: *Jun. 19, 2001

(54) SCINTIGRAPHIC IMAGING AGENTS

(75) Inventors: John Lister-James; Richard T. Dean, both of Bedford, NH (US)

(73) Assignee: Berlex Laboratories, Inc., Montville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/721,443

(22) Filed: Sep. 27, 1996

Related U.S. Application Data

(63) Continuation of application No. 08/439,905, filed on May 12, 1995, now Pat. No. 5,645,815, and a continuation-in-part of application No. 08/253,317, filed on Jun. 3, 1994, now Pat. No. 5,830,856, and a continuation-in-part of application No. 08/210,822, filed on Mar. 18, 1994, now abandoned, which is a continuation-in-part of application No. 07/886,752, filed on May 21, 1992, now abandoned, which is a continuation-in-part of application No. 07/653,012, filed on Feb. 8, 1991, now abandoned, said application No. 08/439,905, is a continuation of application No. 08/044,825, filed on Apr. 8, 1993, now abandoned, which is a continuation-in-part of application No. 07/653,012.

(51) Int. Cl.$^7$ ............................. A61K 51/00; A61M 36/14

(52) U.S. Cl. ................... 424/1.11; 514/331; 514/332; 514/333; 514/336; 435/7.1; 424/1.52; 424/1.65; 424/1.69; 424/9.1; 546/22; 546/233; 546/268

(58) Field of Search ................... 435/7.1; 424/1, 424/11, 1.57, 1.65, 1.69, 9.1; 514/183, 210, 225, 318, 326, 331, 332, 333, 336, 340, 341, 342, 343, 374, 376, 381, 383, 397, 401; 546/22, 232, 268, 193, 216, 275, 200, 201, 276, 704, 221, 208, 210

(56) References Cited

U.S. PATENT DOCUMENTS

| | | | |
|---|---|---|---|
| 4,578,079 | 3/1986 | Ruoslahti et al. | 623/11 |
| 4,636,380 | 1/1987 | Wong | 424/1.53 |
| 4,732,864 | 3/1988 | Tolman | 424/1.45 |
| 4,732,974 | 3/1988 | Nicolotti et al. | 530/391.5 |
| 4,792,525 | 12/1988 | Ruoslathi et al. | 435/240 |
| 4,861,869 | 8/1989 | Nicolotti et al. | 424/1.53 |
| 5,057,302 | 10/1991 | Johnson et al. | 424/1.65 |
| 5,082,930 | 1/1992 | Nicolotti et al. | 424/1.53 |
| 5,086,069 | 2/1992 | Klein et al. | 514/399 |
| 5,089,249 | 2/1992 | Fritzberg et al. | 534/10 |
| 5,190,920 | 3/1993 | Eyal et al. | 514/17 |
| 5,277,893 | 1/1994 | Rhodes | 424/1.69 |
| 5,326,856 | 7/1994 | Coughlin et al. | 534/14 |
| 5,328,840 | 7/1994 | Coller et al. | 435/240.2 |
| 5,371,184 | 12/1994 | Rajagopalan et al. | 530/324 |
| 5,372,933 | 12/1994 | Zamarron et al. | 435/7.21 |
| 5,380,646 | 1/1995 | Knight et al. | 424/1.69 |
| 5,393,512 | 2/1995 | Vander heyden et al. | 424/1.11 |
| 5,395,609 | 3/1995 | Stuttle et al. | 424/1.69 |
| 5,443,815 | 8/1995 | Dean et al. | 424/1.41 |
| 5,443,816 | 8/1995 | Zamora et al. | 424/1.69 |
| 5,449,761 | 9/1995 | Belinka et al. | 534/10 |
| 5,476,644 | 12/1995 | Illig et al. | 424/1.11 |
| 5,506,208 | 4/1996 | Eyal et al. | 514/17 |
| 5,508,020 | 4/1996 | Dean et al. | 424/1.69 |
| 5,645,815 | * 7/1997 | Dean et al. | 424/1.69 |

FOREIGN PATENT DOCUMENTS

| | | |
|---|---|---|
| 063002 | 10/1982 | (EP) . |
| 108406 | 5/1984 | (EP) . |
| 163119 | 12/1985 | (EP) . |
| 188256 | 7/1986 | (EP) . |
| 372486 | 6/1990 | (EP) . |
| 89122396 | 6/1990 | (EP) . |
| 410537 | 1/1991 | (EP) . |
| 410539 | 1/1991 | (EP) . |
| 410540 | 1/1991 | (EP) . |
| 410541 | 1/1991 | (EP) . |
| 411833 | 2/1991 | (EP) . |
| 422937 | 4/1991 | (EP) . |
| 422938 | 4/1991 | (EP) . |
| 425212 | 5/1991 | (EP) . |
| 453082 | 10/1991 | (EP) . |
| 502536 | 3/1992 | (EP) . |
| 0 478 363 | * 4/1992 | (EP) . |
| 478328 | 4/1992 | (EP) . |
| 512829 | 11/1992 | (EP) . |
| 513810 | 11/1992 | (EP) . |
| 93309924 | 5/1993 | (EP) . |
| WO8900051 | 1/1989 | (WO) . |
| WO8902752 | 4/1989 | (WO) . |
| WO8905150 | 6/1989 | (WO) . |
| WO8910135 | 11/1989 | (WO) . |
| WO8910759 | 11/1989 | (WO) . |
| WO8912680 | 12/1989 | (WO) . |
| WO9010463 | 9/1990 | (WO) . |

(List continued on next page.)

OTHER PUBLICATIONS

Fritzberg et al., "Specific and Stable Labeling of Anti–bodies with technetium–99m with a diamide dithioate chelating agent," *Proc. Natl. Acad. Sci.* 85:4025–4029 (1988).

Parise & Phillips, "Reconstitution of the Purified Platelet Fibrinogen Receptor: Fibrinogen Binding Properties of the Glycoprotein IIb–IIIa Complex," *J. Biol. Chem.* 260:10698–10707 (1985).

Knight, "Radiopharmceuticals for Thrombus Detection," *Sem. Nucl. Med.* 20:52–67 (1990).

(List continued on next page.)

*Primary Examiner*—Bennett Celsa
(74) *Attorney, Agent, or Firm*—Patricia McDaniels; Tatsuya Ikeda

(57) ABSTRACT

This invention provides scintigraphic imaging agents and reagents for preparing said agents, methods for radiolabeling said reagents and kits containing non-radioactive reagents and other components for the convenient preparation of the scintigraphic imaging agents. More specifically, the invention provides scintigraphic imaging agents that are radiolabeled compounds which bind with high affinity to GPIIb/IIIa receptors on activated platelets and using such radiolabeled compounds derivatives to image sites in a mammalian body.

13 Claims, No Drawings

U.S. PATENT DOCUMENTS

| | | |
|---|---|---|
| WO9015818 | 12/1990 | (WO) . |
| WO9101331 | 2/1991 | (WO) . |
| WO9102750 | 3/1991 | (WO) . |
| WO9115515 | 10/1991 | (WO) . |
| WO9117173 | 11/1991 | (WO) . |
| WO9205154 | 4/1992 | (WO) . |
| WO9213572 | 8/1992 | (WO) . |
| WO9300095 | 1/1993 | (WO) . |
| WO9308174 | 4/1993 | (WO) . |
| 602900 | 5/1993 | (WO) . |
| WO9310747 | 6/1993 | (WO) . |
| WO9321962 | 11/1993 | (WO) . |
| WO9323085 | 11/1993 | (WO) . |
| WO9325244 | 12/1993 | (WO) . |
| WO9400489 | 1/1994 | (WO) . |
| WO9419024 | 9/1994 | (WO) . |
| WO9422494 | 10/1994 | (WO) . |
| WO9423758 | 10/1994 | (WO) . |
| WO9525720 | 9/1995 | (WO) . |
| WO9529708 | 11/1995 | (WO) . |
| WO8912625 | 12/1995 | (WO) . |
| WO9533496 | 12/1995 | (WO) . |
| WO9533498 | 12/1995 | (WO) . |

OTHER PUBLICATIONS

Ojima et al., "Design and Synthesis of New RGD Peptides as Inhibitors of Human Platelet Aggregation," i $204^{th}$ Meeting, Amer. Chem. Soc. Abst. 44, 1992.

Hartman et al., "Non–peptide Fibrinogen Receptor Antagonists. 1. Discovery and Design of Exosite Inhibitors," J. Med. Chem. 35:4640–4642 (1992).

Baidoo & Lever, "Synthesis of a Diaminedithiol Bifunctional Chelating Agent For Incorporation of Technetium–99m into Biomolecules," Bioconjugate Chem. 1:132–137 (1990).

Bryson et al., "Protecting Groups in the Preparation of Thiolate Complexes of Technetium," Inorganic Chem. 29:2948–2951 (1990).

Pearson et al., "Thrombus imaging using technetium–99m–labeled high–potency GPIIb/IIIa receptor antagonists. Chemistry and initial biological studies," J. Med. Chem. 39:1372–1382 (1996).

Stevens & Gillis, "Epoxyethers. XI. O→O Acyl Migrations with α–Hydroxyacylals," J. Amer. Chem. Soc. 79:3448–3451 (1957).

DiZio et al., "Progestin–Rhenium Complexes: Metal–Labeled Steroids with High Receptor Binding Affinity, Potential Receptor–Directed Agents for Diagnostic Imaging or Therapy," Bioconjugate Chem. 2:353 (1991).

Corbin et al., "1–Alkyl– (or aryl–) amino–2–methylpropane–2–thiols. Some Bi– and Tetradentate Nitrogen–Sulfur Ligands from Schiff's Base Disulfides," J. Org. Chem. 41:489 (1976).

Zucker, "Platelet Aggregation Measured by the Photometric Method," Method in Enzymol. 169:117–133 (1989).

* cited by examiner

SCINTIGRAPHIC IMAGING AGENTS

This application is a continuation-in-part of U.S. patent application Ser. No. 08/210,822, filed Mar. 18, 1994 and now abandoned; which is a continuation-in-part of U.S. patent application Ser. No. 07/886,752, filed May 21, 1992 and now abandoned; which is a continuation-in-part of U.S. patent application Ser. No. 07/653,012, filed Feb. 8, 1991 and now abandoned; this application is also a continuation-in-part of U.S. patent application Ser. No. 08/439,905, filed May 12, 1995 and now U.S. Pat. No. 5,645,815; which is a continuation of U.S. patent application Ser. No. 08/044,825, filed Apr. 8, 1993 and now abandoned; which is a continuation-in-part of U.S. patent application Ser. No. 07/653,012, filed Feb. 8, 1991 and now abandoned; this application is also a continuation-in-part of allowed U.S. patent application Ser. No. 08/253,317, filed Jun. 3, 1994 now U.S. Pat. No. 5,830,856.

BACKGROUND OF THE INVENTION

1. Field of the Invention

This invention relates to scintigraphic imaging agents and reagents for preparing said agents, methods for radiolabeling said reagents and kits containing non-radioactive reagents and other components for the convenient preparation of the scintigraphic imaging agents.

Specifically, the invention relates to scintigraphic imaging agents labeled with gamma-radiation emitting isotopes such as technetium-99m (Tc-99m), reagents that can be labeled with gamma-radiation emitting radioisotopes, methods and kits for making and radiolabeling such reagents, and methods for using said scintigraphic imaging agents to image pathologic sites in a mammalian body.

More specifically, the invention relates to scintigraphic imaging agents that are radiolabeled compounds which bind with high affinty to GPIIb/IIIa receptors on activated platelets and using such radiolabeled compounds to image sites in a mammalian body.

2. Description of the Prior Art

Thrombosis and thromboembolism, in particular deep vein thrombosis (DVT) and pulmonary embolism (PE), are common clinical conditions that are associated with significant morbidity and mortality. It has been estimated that in the U.S. approximately 5 million patients experience one or more episodes of DVT per year and that over 500,000 cases of PE occur annually, resulting in 100,000 deaths (Seabold, Society of Nuclear Medicine Annual Meeting 1990). It has also been estimated that over 90% of all pulmonary emboli arise from DVT in the lower extremities.

Anticoagulant therapy can effectively treat these conditions if applied early enough. However, such treatment is associated with risks, such as internal bleeding, that prevent their unnecessary prophylactic application. More advanced techniques of thrombolytic intervention (such as the administration of recombinant tissue plasminogen activator or streptokinase) can be used in acute cases, but these techniques carry even greater risk. Moreover, effective clinical application of these techniques requires that the site of the offending thrombus be identified so as to monitor the effect of treatment.

For these reasons, a rapid means of detecting and localizing thrombi in vivo, most preferably using non-invasive methods, is highly desirable. Methods currently utilized for the identification of sites of DVT are contrast venography and compression B-mode ultrasound; the choice of which technique is used depends on the expected location of the thrombus. The currently-available techniques are unsatisfactory, however, because in many cases they yield inaccurate results, are uncomfortable for the patient or are otherwise clinically inappropriate. The technique of contrast venography is additionally disadvantageous because it is an invasive technique.

Current methods used to diagnose PE include chest X-ray, electrocardiogram (EKG), arterial oxygen tension, perfusion and ventilation lung scans, and pulmonary angiography. However, none of these methods (except pulmonary angiography) is capable of providing an unequivocal diagnosis, and this method is an invasive method.

One area of medicine concerned with the non-invasive localization of pathologies in vivo is nuclear medicine. In the field of nuclear medicine, pathological conditions are localized, or their extent is assessed, by detecting the specific distribution of small quantities of internally-administered radioactively labeled tracer compounds (called radiotracers, radiopharmaceuticals or scintigraphic imaging agents). Methods for detecting these radiopharmaceuticals are known generally as scintigraphic imaging, radioimaging or radiodiagnostic imaging methods. A variety of radionuclides are known to be useful for radioimaging, including $^{18}F$, $^{64}Cu$, $^{67}Ga$, $^{68}Ga$, $^{99m}Tc$, $^{111}In$, $^{123}I$, $^{125}I$ and $^{131}I$. Of these radionuclides, Tc-99m and In-111 are preferred single photon-emitting radionuclides and Ga-68 is a preferred positron-emitting radionuclide.

A number of factors must be considered for optimal radioimaging in humans. To maximize the efficiency of detection, a radionuclide that emits gamma energy in the 100 to 200 keV range is preferred. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site. Tc-99m is a preferred radionuclide for radioimaging in humans because it emits gamma radiation at 140 keV, it has a physical half-life of 6 hours, and it is readily available on-site using a molybdenum-99/technetium-99m generator.

A gamma-emitting radiotracer that binds specifically to a component of a thrombus in preference to other tissues when administered in vivo would provide an external scintigraphic image to define the location of the thrombus-bound radiotracer and hence the thrombus. Such a radiotracer should strongly and specifically bind to a component of a thrombus in order to achieve specific radioimaging of thrombus sites. The primary components of thrombi to which such a radiotracer might specifically bind are blood cells, largely activated platelets, enmeshed in cross-linked fibrin.

Attempts to provide radiotracers for imaging thrombi are known in the prior art. These include autologous platelets, labeled with either In-111 or Tc-99m, and I-123 and I-125 labeled fibrinogen (the latter detected with a gamma scintillation probe as opposed to a gamma camera). Additional radiolabeled compounds used to label thrombi include plasmin, plasminogen activators, heparin, fibronectin, fibrin Fragment $E^1$ and anti-fibrin and anti-platelet monoclonal antibodies (see Knight, 1990, *Sem. Nucl. Med.* 20: 52–67 for review).

Activated platelets are particularly good targets for radioimaging thrombi because they are not normally found in circulating blood (which contains unactivated platelets). Activated platelets express the GPIIb/IIIa receptor on their cell surfaces which binds to fibrinogen (Parise & Phillips, 1985, *J. Biol. Chem.* 260: 10698–10707). However, small, synthetic analogues have been developed that bind to this receptor (see, for example, Klein et al., 1992, U.S. Pat. No. 5,086,069 and Egbertson et al., 1992, European Patent Application No. EPA 0478328A1). Some of these synthetic molecules bind to the GPIIa/IIIb receptor with very high affinity (see Egbertson et al., ibid.).

Compounds having the ability to bind to the platelet GPIIb/IIIa receptor are known in the prior art.

Ruoslahti & Pierschbacher, U.S. Pat. No. 4,578,079 describe peptides capable of binding to platelets.

Ruoslahti & Pierschbacher, U.S. Pat. No. 4,792,525 describe peptides capable of binding to platelets.

Klein et al., 1992, U.S. Pat. No. 5,086,069 disclose guanidine derivatives that bind to the GPIIb/IIIa receptor.

Pierschbacher et al., 1989, International Patent Application Ser. No. PCT/US88/04403 disclose conformationally-restricted RGD-containing peptides for inhibiting cell attachment to a substratum.

Alig et al, 1989, European Patent Application 89122396.8, disclose benzoic acid and phenylalanine derivatives as fibrinogen antagonists.

Nutt et al., 1990, European Patent Application 90202015.5 disclose cyclic RGD peptides that are fibrinogen receptor antagonists.

Nutt et al., 1990, European Patent Application 90202030.4 disclose cyclic RGD peptides that are fibrinogen receptor antagonists.

Nutt et al., 1990, European Patent Application 90202031.2 disclose cyclic RGD peptides that are fibrinogen receptor antagonists.

Nutt et al., 1990, European Patent Application 90202032.0 disclose cyclic RGD peptides that are fibrinogen receptor antagonists.

Nutt et al., 1990, European Patent Application 90311148.2 disclose cyclic peptides that are fibrinogen receptor antagonists.

Nutt et al., 1990, European Patent Application 90311151.6 disclose cyclic peptides that are fibrinogen receptor antagonists.

Ali et al., 1990, European Patent Application 90311537.6 disclose cyclic peptides that are fibrinogen receptor antagonists.

Barker et al., 1991, International Patent Application Ser. No. PCT/US90/03788 disclose cyclic peptides for inhibiting platelet aggregation.

Pierschbacher et al., 1991, International Patent Application Ser. No. PCT/US91/02356 disclose cyclic peptides that are fibrinogen receptor antagonists.

Egbertson et al., 1992, European Patent Application 0478328A1 disclose tyrosine derivatives that bind with high affinity to the GPIIb/IIIa receptor.

Duggan et al, 1992, European Patent Application 92304111.5 disclose fibrinogen receptor antagonists.

Garland et al, 1992 European Patent Applications 92103861.8 and 92108214.5 disclose phenylamide derivatives as platelet aggregation inhibitors.

Bondinell et al, 1993, International Patent Application Ser. No. PCT/US92/05463 disclose bicyclic fibrinogen antagonists.

Blackburn et al., 1993, International Patent Application Ser. No. PCT/US92/08788, disclose nonpeptidyl integrin inhibitors having specificity for the GPIIb/IIIa receptor.

Hartman et al., 1993, European Patent Application Ser. No. 93309924.6 disclose fibrinogen receptor antagonists.

Ojima et al., 1992, 204th Meeting, Amer. Chem. Soc. Abst. 44 disclose synthetic multimeric RDGF peptides useful in inhibiting platelet aggregation.

Hartman et al., 1992, J. Med. Chem. 35: 4640–4642 describe tyrosine derivatives that have a high affinity for the GPIIb/IIIa receptor.

Radiolabeled peptides for radioimaging thrombi also have been reported in the prior art.

Stuttle, 1990, International Patent Application Ser. No. PCT/GB90/00933 discloses radioactively labeled peptides containing from 3 to 10 amino acids comprising the sequence arginine-glycine-aspartic acid (RGD), capable of binding to an RGD binding site in vivo.

Rodwell et al., 1991, International Patent Application Ser. No. PCT/US91/03116 disclose conjugates of "molecular recognition units" with "effector domains".

Maraganore et al., 1991, International Patent Application Ser. No. PCT/US90/04642 disclose a radiolabeled thrombin inhibitor comprising (a) a inhibitor moiety; (b) a linker moiety; and (c) an "anion binding exosite (ABE)" moiety.

The use of chelating agents for radiolabeling peptides, and methods for labeling peptides with Tc-99m are known in the prior art and are disclosed in co-pending U.S. patent applications Ser. Nos. 07/653,012, now abandoned, which issued as U.S. Pat. No. 5,654,272; 07/807,062, now U.S. Pat. No. 5,443,815; 07/871,282, a divisional of which issued as U.S. Pat. No. 5,720,934; 07/886,752, now abandoned, a continuation of which has been allowed as U.S. Ser. No. 08/273,274; 07/893,981, now U.S. Pat. No. 5,508,020; and radiolabeled peptides for use as scintigraphic imaging agents for imaging thrombi are known in the prior art and are disclosed in co-pending U.S. patent applications Ser. Nos. 07/886,752, now abandoned, a continuation of which has been allowed as U.S. Ser. No. 08/273,274; 07/893,981, now U.S. Pat. No. 5,508,020; and 08/044,825, now abandoned, which issued as U.S. Pat. No. 5,645,815 which are hereby incorporated by reference.

There remains a need for small (to enhance blood and background tissue clearance), synthetic (to make routine manufacture practicable and to ease regulatory acceptance), high-affinity, specific-binding molecules radiolabeled with a convenient radiolabel, preferably Tc-99m, for use in imaging thrombi in vivo. Small synthetic compounds that bind specifically to the GPIIb/IIIa receptor expressed on the cell surface of activated platelets, and that are radiolabeled with a convenient radioisotope, preferably Tc-99m, fulfill this need in the art.

SUMMARY OF THE INVETION

This invention provides small, synthetic, radiolabeled (preferably with Tc-99m) compounds that bind to the GPIIb/IIIa receptor with high affinity, for use as scintigraphic agents for non-invasive imaging of thrombi in vivo. In particular, the invention provides small synthetic compounds that bind specifically to the GPIIb/IIIa receptor on activated platelets, that are radiolabeled with a convenient radioisotope, preferably Tc-99m, and that are inherently more stable than radiolabeled peptides in vivo.

The present invention provides radioactively-labeled scintigraphic thrombus imaging agents. Specifically, the invention provides reagents for preparing such scintigraphic imaging agents that are radiolabeled with a gamma-emitting radioisotope, preferably Tc-99m. The reagents of the invention are each comprised of a specific binding compound that binds specifically and with high affinity to the platelet GPIIb/IIIa receptor, covalently linked to a radiolabel-binding moiety.

For optimal imaging, the reagent must be capable of binding to the platelet GPIIb/IIIa receptor with sufficient affinity so as to be capable of inhibiting adenosine diphosphate (ADP)-induced aggregation of human platelets by 50% in a standard, in vitro platelet aggregation assay (see Example 11 below) at a reagent concentration of no more than 1.0 μM. Also, it is of distinct commercial advantage to use small compounds, preferably having a molecular weight of less than about 10,000 daltons, that can be readily manufactured using conventional, well-established and economical techniques. Additionally, and advantageously, such compounds are more likely not to be immunogenic and to clear rapidly from the vasculature, thus facilitating better and more rapid imaging of thrombi. Conversely, larger molecules such as antibodies or antibody fragments, or other biologically-derived peptides larger than about 10,000 daltons, are more costly to manufacture and are more likely to be immunogenic and to clear more slowly from the bloodstream, thereby interfering with rapid diagnoses of the existence and localization of thrombi in vivo.

The present invention provides reagents for preparing scintigraphic thrombus imaging agents which are tyrosine derivatives of the formula:

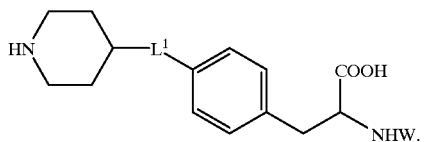

Ia and;

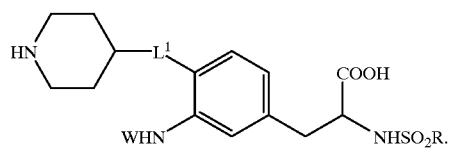

Ib wherein $L^1$ is a bivalent radical selected from the group consisting of -$(CR_2)_5$-, —O-$(CR_2)_4$-, -$(CR_2)_4$-O—, —O-$(CR_2)_2$-O-$(CR_2)_2$-,-$(CR_2)_2$-O-$(CR_2)_2$O—, —O-$(CR_2)_3$-O—, —NHC(O)-$(CR_2)_3$-,—NHC(O)-$CR_2$-O—$CR_2$-, NHC(O)-$(CR_2)_2$-O—, —$CR_2$-NHC(O)-$(CR_2)_2$-, —$CR_2$-NHC(O)-$CR_2$-O—, -$(CR_2)_2$-NHC(O)-$CR_2$-, -$(CR_2)_3$-NHC(O)-, —O-$(CR_2)$-NHC(O)-, —C(O)NH-$(CR_2)_3$-, —C(O)NH-$(CR_2)_2$-O—, —$CR_2$-C(O)NH-$(CR_2)_2$-, -$(CR_2)_2$-C(O)NH—$CR_2$-, —O-$(CR_2)$-C(O)NH—$CR_2$-, -$(CR_2)_3$-C(O)NH—, —O-$(CR_2)_2$-C(O)NH—, —$CR_2$-O—$CR_2$-C(O)NH—, wherein each R is independently H or lower alkyl, and two geminal R groups may be taken together as a lower alkylidene; W is a radiolabel binding moiety having a molecular weight less than about 500 Daltons, wherein the reagent binds to the platelet glycoprotein IIb/IIIa receptor, and which reagent is capable of inhibiting by 50% ADP-induced aggregation of human platelets in platelet-rich plasma in vitro when said reagent is present at a concentration of not more than about 1.0 μM. In preferred embodiments, the radiolabel binding moiety is complexed with a detectable gamma radiation-emitting radioisotope, for example, $^{18}$F, $^{64}$Cu, $^{67}$Ga, $^{68}$Ga, $^{99m}$Tc, $^{111}$In, $^{123}$I, $^{125}$I and $^{131}$I, preferably Tc-99m. The unradiolabeled reagents, as well as the radiolabeled embodiments of such reagents, are explicitly provided by the invention. Additionally, methods of preparing the scintigraphic imaging agents of the invention from the reagents of the invention are provided, as well as methods for using the radiolabeled scintigraphic imaging agents of the invention for the non-invasive detection and localization of thrombus sites in vivo.

The invention also provides reagents for preparing scintigraphic thrombus imaging agents comprising specific binding compounds which are tyrosine derivatives that specifically bind to the platelet GPIIb/IIIa receptor, and that are covalently linked to a radiolabel-binding moiety, the reagents having the formula:

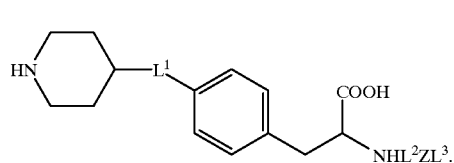

IIa and;

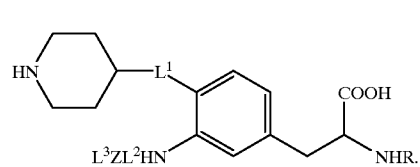

IIb wherein $L^1$ is a bivalent radical selected from the group consisting of -$(CR_2)_5$-, —O-$(CR_2)_4$-, -$(CR_2)_4$-O—,—O-$(CR_2)_2$-O-$(CR_2)_2$-,-$(CR_2)_2$-O-$(CR_2)_2$-O—,—O-$(CR_2)_3$-O—,—NHC(O)-$(CR_2)_3$-,—NHC(O)-$CR_2$-O—$CR_2$-, NHC(O)-$(CR_2)_2$-O—, —$CR_2$-NHC(O)-$(CR_2)_2$-, —$CR_2$-NHC(O)-$CR_2$-O—, -$(CR_2)_2$-NHC(O)-$CR_2$-, -$(CR_2)_3$-NHC(O)-, —O-$(CR_2)_2$-NHC(O)-, —C(O)NH-$(CR_2)_3$-, —C(O)NH-$(CR_2)_2$-O—, —$CR_2$-C(O)NH-$(CR_2)_2$-, -$(CR_2)_2$-C(O)NH—$CR_2$-, —O-$(CR_2)_2$-C(O)NH—$CR_2$-, -$(CR_2)_3$-C(O)NH-, —O-$(CR_2)_2$-C(O)NH—, —$CR_2$-O—$CR_2$-C(O)NH—, wherein each R is independently H or lower alkyl, and two geminal R groups may be taken together as a lower alkylidene; $L^2$ is either nothing or is a bivalent spacer radical, preferably an amino acid or a peptide comprised of from about 2 to about 4 amino acids; and $L^3$ is nothing or is an —OH group, an —$NH_2$ group, an amino acid or amino acid amide, or a peptide comprised of from about 2 to 4 amino acids; and wherein Z is a radiolabel-binding moiety, wherein the reagent binds to the platelet glycoprotein IIb/IIIa receptor, and which reagent is capable of inhibiting by 50% ADP-induced aggregation of human platelets in platelet-rich plasma in vitro when said reagent is present at a concentration of not more than about 1.0 μM. In preferred embodiments, the radiolabel binding moiety is complexed with a detectable gamma radiation-emitting radioisotope, wherein the reagent binds to the platelet glycoprotein IIb/IIIa receptor, and which reagent is capable of inhibiting by 50% ADP-induced aggregation of human platelets in platelet-rich plasma in vitro when said reagent is present at a concentration of not more than about 1.0 μM. In preferred embodiments, the radiolabel binding moiety is complexed with a detectable gamma radiation-emitting radioisotope, for example, $^{18}$F, $^{64}$Cu, $^{67}$Ga, $^{68}$Ga, $^{99m}$Tc, $^{111}$In, $^{123}$I, $^{125}$I and $^{131}$I, preferably Tc-99m. The unradiolabeled reagents, as well as the radiolabeled embodiments of such reagents, are explicitly provided by the invention. Additionally, methods of preparing the scintigraphic imaging agents of the invention from the reagents of the invention are provided, as well as methods for using the radiolabeled scintigraphic imaging agents of the invention for the non-invasive detection and localization of thrombus sites in vivo.

The invention also comprises scintigraphic imaging agents that are complexes of the reagents of the invention with a radioisotope. In one embodiment of this aspect of the invention, the radioisotope is a radioactive halogen, for example, $^{18}F$, $^{123}I$, $^{125}I$ or $^{131}I$, and the radiolabel binding moiety has the formula:

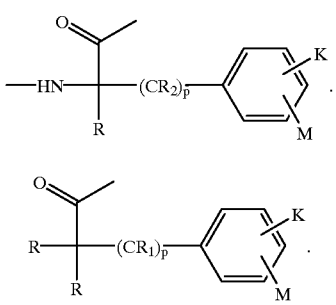

IIIa

IIIb where p is an integer from 0 to 4, K is —I or —SnR$_3$ and M is H, OH or OR, where each R is independently H, $C_1$ to $C_4$ alkyl, or aryl. In preferred embodiments, K is —Sn (butyl)$_3$ and M is H.

In another embodiment of this aspect of the invention, the radioisotope is $^{64}Cu$, $^{67}Ga$, $^{68}Ga$, or $^{111}In$, preferably $^{111}In$, and the radiolabel binding moiety has the formula that is:

a bisamino bisthiol moiety having a formula [for purposes of this invention, radiolabel-binding moieties having these structures will be referred to as "BAT" moieties]

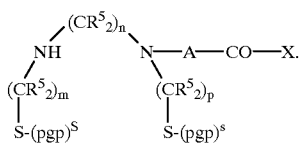

VII wherein each $R^5$ can be independently H, methyl or ethyl; each (pgp)$^S$ can be independently a thiol protecting group or H; m, n and p are each integers that are independently 2 or 3; A is linear or cyclic lower alkyl, aryl, heterocyclyl, combinations or substituted derivatives thereof, and X is a covalent linkage to $L^2$; or

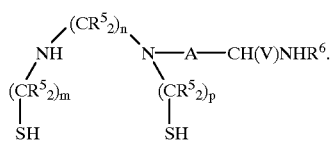

VIII wherein each $R^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or carbonyl covalently linked to $L^2$; $R^6$ is H or a covalent linkage to $L^2$; provided that when V is H, $R^6$ is a covalent linkage to $L^2$ and when $R^6$ is H, V is a carbonyl covalently linked to $L^2$;

a bisamino bisthiol moiety having a formula (for purposes of this invention, radiolabel-binding moieties having these structures will be referred to as "CAT" moieties)

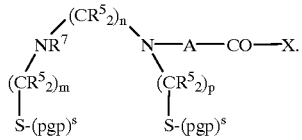

IX wherein each $R^5$ can be independently H, methyl or ethyl; each (pgp)$^S$ can be independently a thiol protecting group or H; m, n and p are independently 2 or 3; A is linear or cyclic lower alkyl, aryl, heterocyclyl, combinations or substituted derivatives thereof; $R^7$ is $C_1$–$C_4$ alkyl; and X is a covalent linkage to $L^2$; or

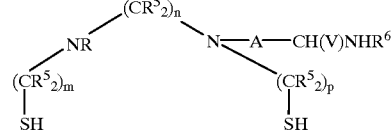

X.

wherein each $R^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or carbonyl covalently linked to $L^2$; $R^6$ is H or a covalent linkage to $L^2$; $R^7$ is $C_1$–$C_4$ alkyl; provided that when V is H, $R^6$ is a covalent linkage to $L^2$ and when $R^6$ is H, V is a carbonyl covalently linked to $L^2$;

or diethylenetriaminepentaacetic acid (DTPA)

$(HOOCCH_2)_2N(CR_2)(CR_2)N(CH_2COOH)(CR_2)(CR_2)N(CH_2COOH)_2$ or ethylenediaminetetraacetic acid (EDTA)

$(HOOCCH_2)_2N(CR_2)(CR_2)N(CH_2COOH)_2$ where each R is independently H, $C_1$ to $C_4$ alkyl, or aryl and one R is covalently linked to $L^1$; or 1,4,7,10-tetraazadodecanetetraacetic acid

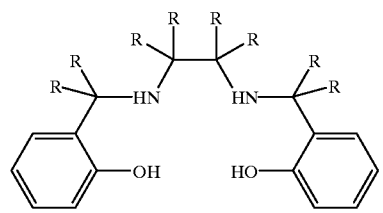

R=H or lower alkyl and one R is a covalent linkage to $L^1$;

or

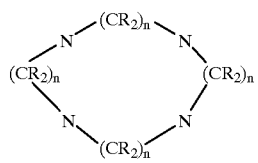

where n is an integer that is 2 or 3 and where each R is independently H, $C_1$ to $C_4$ alkyl, or aryl and one R is covalently linked to $L^2$; or desferrioxamine.

In another embodiment of this aspect of the invention, the radioisotope is Tc-99m, and the radiolabel binding moiety has a formula that is:

IVa. -(amino acid)$^1$-(amino acid)$^2$-(amino thiol),

IVb. -(mercaptocarboxylic acid)-(amino acid)$^1$-(amino acid)$^2$,

IVc. -(a primary α,ω or β,ω-diamino acid)$^1$-(amino acid)-(amino thiol), or

IVd. -(mercaptocarboxylic acid)-(amino acid)$^1$-(a primary α,ω- or β,ω-diamino acid)

wherein (amino acid)$^1$ and (amino acid)$^2$ are each independently any naturally-occurring, modified, substituted or altered primary α- or β-amino acid not comprising a thiol group;

(amino thiol) is selected from the group consisting of cysteine, isocysteine, homocysteine, penicillamine, 2-mercaptoethylamine, and 3-mercaptopropylamine; and (mercaptocarboxylic acid) is selected from the group consisting of cysteine, isocysteine, homocysteine, penicillamine, 2-mercaptoacetic acid, and 3-mercaptopropionic acid; or V. -Cys(pgp)-(amino acid)-Cys(pgp)-, where (amino acid) is any naturally-occurring, modified, substituted or altered α- or β-amino acid and (pgp) is a thiol protecting group; or a bisamido, bisthiol moiety having a formula VIa. $(pgp)^S(CR^1{}_2)_qC(O)NH(CR^1{}_2)_rNHC(O)(CR^1{}_2)_s(pgp)^S$ or VIb. $(pgp)^S(CR^1{}_2)_tNHC(O)(CR^1{}_2)_uNHC(O)(CR^1{}_2)_s(PgP)^S$, or an amido amino bisthiol moiety having a formula VIc. $(pgp)^S(CR^1{}_2)_tNH(CR^1{}_2)_rNHC(O)(CR^1{}_2)_s(pgp)^S$ or VId. $(pgp)^S(CR^1{}_2)_tNHC(O)(CR^1{}_2)_uNH(CR^1{}_2)_v(pgp)^S$ wherein $R^1$ is each independently H, $C_1$ to $C_4$ alkyl, or aryl, and one $R^1$ is linked to $L^2$, and q is an integer that is either 1 or 2, r is an integer that is either 2 or 3, s is an integer that is either 1 or 2, t is an integer that is either 2 or 3, u is an integer that is either 1 or 2, and v is an integer that is either 2 or 3; or a bisamino bisthiol moiety having a formula [for purposes of this invention, radiolabel-binding moieties having these structures will be referred to as "BAT" moieties]

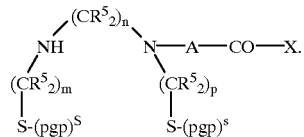

VII wherein each $R^5$ can be independently H, methyl or ethyl; each $(pgp)^S$ can be independently a thiol protecting group or H; m, n and p are each integers that are independently 2 or 3; A is linear or cyclic lower alkyl, aryl, heterocyclyl, combinations or substituted derivatives thereof; and X is a covalent linkage to $L^2$; or

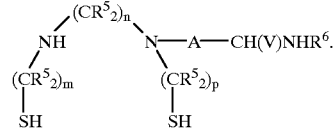

VIII wherein each $R^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or carbonyl covalently linked to $L^2$; $R^6$ is H or a covalent linkage to $L^2$; provided that when V is H, $R^6$ is a covalent linkage to $L^2$ and when $R^6$ is H, V is a carbonyl covalently linked to $L^2$;

a bisamino bisthiol moiety having a formula (for purposes of this invention, radiolabel-binding moieties having these structures will be referred to as "CAT" moieties)

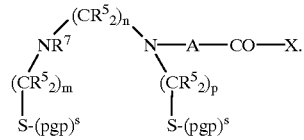

IX wherein each $R^5$ can be independently H, methyl or ethyl; each $(pgp)^S$ can be independently a thiol protecting group or H; m, n and p are independently 2 or 3; A is linear or cyclic lower alkyl, aryl, heterocyclyl, combinations or substituted derivatives thereof; $R^7$ is $C_1$–$C_4$ alkyl; and X is a covalent linkage to $L^2$; or

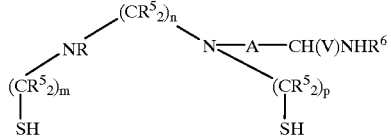

X.

wherein each $R^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or carbonyl covalently linked to $L^2$; $R^6$ is H or a covalent linkage to $L^2$; $R^7$ is $C_1$–$C_4$ alkyl; provided that when V is H, $R^6$ is a covalent linkage to $L^2$ and when $R^6$ is H, V is a carbonyl covalently linked to $L^2$;

or a diamino dioxime having the formula:

where each $R^8$ is independently H, $C_1$ to $C_4$ alkyl, or aryl and one $R^8$ is covalently linked to $L^2$;
or a bis-thiosemicarbazone which has a formula:

where n is an integer that is 0 or 1 and where each R is independently H, $C_1$ to $C_4$ alkyl, or aryl and one R is covalently linked to $L^2$; or

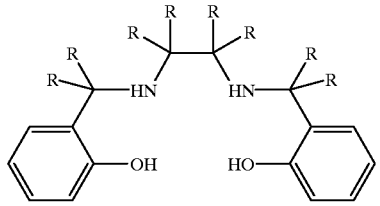

R=H or lower alkyl and one R is a covalent linkage to $L^1$;

or

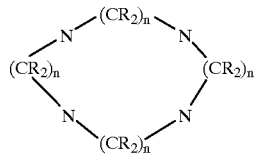

where n is an integer that is 2 or 3 and where each R is independently H, $C_1$ to $C_4$ alkyl, or aryl and one R is covalently linked to $L^2$.

Methods for radiolabeling the reagents of the invention are provided to produce the radiolabeled, preferably Tc-99m radiolabeled, complexes of the invention. Such complexes are formed by reacting the reagents of the invention with Tc-99m in the presence of a reducing agent, preferably dithionite ion, stannous ion or ferrous ion. Complexes of the invention are also formed by labeling the reagents of the invention with Tc-99m by ligand exchange of a prereduced complex as provided herein.

The invention also provides kits for preparing scintigraphic imaging agents that are the reagents of the invention radiolabeled with Tc-99m. Kits for Tc-99m labeling of the reagents provided by the invention are comprised of a sealed vial containing a predetermined quantity of a reagent of the invention and a sufficient amount of reducing agent to label the reagent with Tc-99m.

This invention provides methods for using scintigraphic imaging agents that are radiolabeled reagents for imaging thrombi within a mammalian body by obtaining in vivo gamma scintigraphic images. These methods comprise administering an effective diagnostic amount of scintigraphic imaging agents of the invention and detecting the gamma radiation emitted by the radiolabel localized at the thrombus site within the mammalian body.

It will also be recognized by those having skill in the relevant arts that thrombi are commonly found at sites of atherosclerotic plaque; that integrin receptors that may bind to the scintigraphic imaging agents of the invention may be found in certain tumors; and that such integrin receptors are involved in cell adhesion processes that accompany or initiate leukocyte localization at sites of infection. Therefore it will be recognized that the scintigraphic imaging agents of this invention have additional utility as imaging agents for imaging sites in which the GPIIb/IIIa receptor is expressed, including atherosclerotic plaques, tumors and sites of infection.

Specific preferred embodiments of the present invention will become evident from the following more detailed description of certain preferred embodiments and the claims.

DETAILED DESCRIPTION OF THE INVENTION

The present invention provides reagents for preparing radiolabeled thrombus imaging agents for imaging a thrombus within a mammalian body. The reagents provided by the invention comprise a radiolabel binding moiety covalently linked to a specific binding compound which specifically binds to a platelet receptor that is the platelet GPIIb/IIIa receptor and is capable of inhibiting by 50% aggregation of human platelets in platelet-rich plasma when present at a concentration of no more than 1.0 $\mu$M in a standard in vitro assay. For purposes of the invention, the terms "scintigraphic thrombus imaging agent" and scintigraphic imaging agent" is intended to refer to embodiments of the invention comprising a specific binding compound, for example, a tyrosine derivative, that is covalently linked to a radiolabel binding moiety and radiolabeled, preferably with Tc-99m, In-111 or Ga-68, most preferably with Tc-99m.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{9m}$Tc generator.

In the Tc-99m binding moieties and compounds covalently linked to such moieties that contain a thiol covalently linked to a thiol protecting groups [(pgp)$^S$] provided by the invention, the thiol-protecting groups may be the same or different and may be but are not limited to:

—$CH_2$-aryl (aryl is phenyl or alkyl or alkyloxy substituted phenyl);
—CH-(aryl)$_2$, (aryl is phenyl or alkyl or alkyloxy substituted phenyl);
—C-(aryl)$_3$, (aryl is phenyl or alkyl or alkyloxy substituted phenyl);
—$CH_2$-(4-methoxyphenyl);
—CH-(4-pyridyl)(phenyl)$_2$;
—C(CH$_3$)$_3$
-9-phenylfluorenyl;
—$CH_2$NHCOR (R is unsubstituted or substituted alkyl or aryl);
—$CH_2$-NHCOOR (R is unsubstituted or substituted alkyl or aryl);
—CONHR (R is unsubstituted or substituted alkyl or aryl);
—$CH_2$-S—$CH_2$-phenyl Preferred protecting groups have the formula —$CH_2$-NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

The reagents and scintigraphic imaging agents of the invention are provided having the general structure of formula:

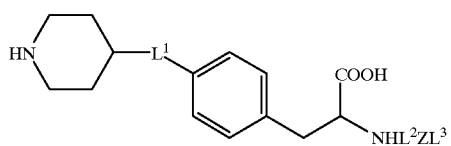

IIa.

and;

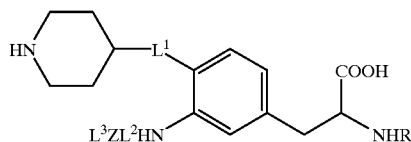

IIb.

Regarding the variable substituents in individual embodiments of the reagents and scintigraphic agents of the invention, $L^1$ is a bivalent radical selected from the group consisting of -(CR$_2$)$_5$-, —O-(CR$_2$)$_4$-, -(CR$_2$)$_4$-O—, —O-(CR$_2$)$_2$-O-(CR$_2$)$_2$-, -(CR$_2$)$_2$-O-(CR$_2$)$_2$-O—, —O-(CR$_2$)$_3$-O—, —NHC(O)-(CR$_2$)$_3$-, —NHC(O)-CR$_2$-O—CR$_2$-, NHC(O)-(CR$_2$)$_2$-O—, —CR$_2$-NHC(O)-(CR$_2$)$_2$-, —CR$_2$-NHC(O)-CR$_2$-O—, -(CR$_2$)$_2$-NHC(O)-CR$_2$-, -(CR$_2$)$_3$-NHC(O)-, —O-(CR$_2$)-NHC(O)-, —C(O)NH-(CR$_2$)$_3$-, —C(O)NH-(CR$_2$)$_2$-O—, —CR$_2$-C(O)NH-(CR$_2$)$_2$-, -(CR$_2$)$_2$-C(O)NH-CR$_2$-, —O-(CR$_2$)-C(O)NH—CR$_2$-, -(CR$_2$)$_3$-C(O)NH—, —O-(CR$_2$)$_2$-C(O)NH—, —CR$_2$-O—CR$_2$-C(O)NH—, wherein each R is independently H or lower alkyl, and two geminal R groups may be taken together as a lower alkylidene. Also additionally, $L^2$ is either nothing or is a bivalent spacer radical, preferably an amino acid or a peptide comprised of from about 2 to about 4 amino acids. Additionally, $L^2$ can also be any of the following, non-limiting list of bivalent radicals: -(CR$_2$)$_6$-, —CR$_2$C(O)-, —CR=CR—, —C≡C—, or -(CR$_2$)$_n$(Ar)$_s$V(Ar)$_s$(CR$_2$)m-, where n is an integer from 1 to 6, m is an integer from 0 to 6 and wherein the sum of n and m is no greater than 6, s is an integer that is either 0 or 1; (Ar) is a 1,2-, 1,3- or 1,4-linked benzene ring, and V is either nothing or is an oxygen atom, a sulfur atom, NH, C(O), NRC(O), C(O)NR, NRSO$_2$, SO$_2$NH, OC(O), C(O)O, or NRC(S)NR, where each R is independently H, $C_1$ to $C_4$ alkyl, or aryl.

Also in individual embodiments of the reagents and scintigraphic agents of the invention, $L^3$ is either nothing or is an —OH group, an —NH$_2$ group, an amino acid or amino acid amide, or a peptide comprised of from about 2 to 4 amino acids.

The reagents and scintigraphic imaging agents provided by the invention are comprised of specific binding compounds that specifically bind to the platelet GPIIb/IIIa receptor, covalently linked to a radiolabel-binding moiety, designated herein as Z in the above formulae. As provided by the invention, the radiolabel binding moieties comprising the reagents and scintigraphic imaging agents of the invention include but are not limited to radiolabel binding moieties having the formula:

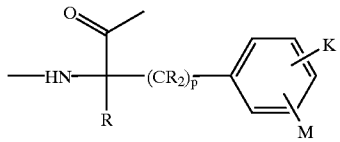

IIIa.

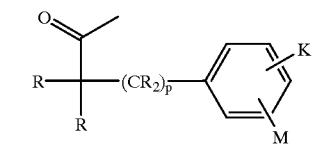

IIIb.

where p is an integer from 0 to 4, K is —I or —SnR$_3$ and M is H, OH or OR, where each R is independently H, $C_1$ to $C_4$ alkyl, or aryl; and IVa. -(amino acid)$^1$-(amino acid)$^2$-(amino thiol), IVb. -(mercaptocarboxylic acid)-(amino acid)$^1$-(amino acid)$^2$, IVc. -(a primary α,ω- or β,ω-diamino acid)$^1$-(amino acid)-(amino thiol), or IVd. -(mercaptocarboxylic acid)-(amino acid)$^1$-(a primary α,ω- or β,ω-diamino acid)

wherein (amino acid)$^1$ and (amino acid)$^2$ are each independently any naturally-occurring, modified, substituted or altered primary α- or β-amino acid not comprising a thio group; (amino thiol) is selected from the group consisting of cysteine, isocysteine, homocysteine, penicillamine, 2-mercaptoethylamine, and 3-mercaptopropylamine; and (mercaptocarboxylic acid) is selected from the group consisting of cysteine, isocysteine, homocysteine, penicillamine, 2-mercaptoacetic acid, and 3-mercaptopropionic acid; and V. -Cys(pgp)-(amino acid)-Cys(pgp)-, where (amino acid) is any naturally-occurring, modified, substituted or altered primary α- or β-amino acid and (pgp) is a thiol protecting group; and a bisamido, bisthiol moiety having a formula VIa. (pgp)$^S$(CR$^1_2$)$_q$C(O)NH(CR$^1_2$)$_r$NHC(O)(CR$^1_2$)$_s$(pgp)$^S$ or VIb. (pgp)$^S$(CR$^1_2$)$_t$NHC(O)(CR$^1_2$)$_u$NHC(O)(CR$^1_2$)$_s$(pgp)$^S$, or an amido amino bisthiol moiety having a formula VIc. (pgp)$^S$(CR$^1_2$)$_t$NH(CR$^1_2$)$_r$NHC(O)(CR$^1_2$)$_s$(pgp)$^S$ or VId. (pgp)$^S$(CR$^1_2$)$_t$NHC(O)(CR$^1_2$)$_u$NH(CR$^1_2$)$_v$(pgp)$^S$ wherein each $R^1$ is independently H, $C_1$ to $C_4$ alkyl, or aryl, and one $R^1$ is linked to $L^2$, and q is an integer that is either 1 or 2, r is an integer that is either 2 or 3, s is an integer that is either 1 or 2, t is an integer that is either 2 or 3, u is an integer that is either 1 or 2, and v is an integer that is either 2 or 3; and a bisamino bisthiol moiety having a formula [for purposes of this invention, radiolabel-binding moieties having these structures will be referred to as "BAT" moieties]

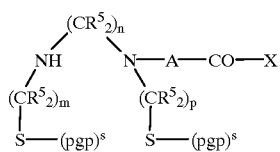
VII.

wherein each $R^5$ can be independently H, methyl or ethyl; each $(pgp)^S$ can be independently a thiol protecting group or H; m, n and p are each an integer that is independently 2 or 3; A is linear or cyclic lower alkyl, aryl, heterocyclyl, combinations or substituted derivatives thereof; and X is a covalent linkage to $L^2$; or

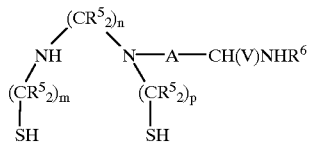
VIII.

wherein each $R^5$ is independently H, lower alkyl having 1 to 6 carbon atoms, phenyl, or phenyl substituted with lower alkyl or lower alkoxy; m, n and p are each an integer that is independently 1 or 2; A is linear or cyclic lower alkyl, aryl, heterocyclyl, combinations or substituted derivatives thereof; V is H or carbonyl covalently linked to $L^2$, $R^6$ is H or a covalent linkage to $L^2$, provided that when V is H, $R^6$ is a covalent linkage to $L^2$ and when $R^6$ is H, V is a carbonyl covalently linked to $L^2$; and a bisamino bisthiol moiety having a formula (for purposes of this invention, radiolabel-binding moieties having these structures will be referred to as "CAT" moieties)

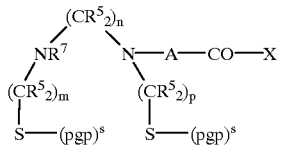
IX.

wherein each $R^5$ can be independently H, methyl or ethyl; each $(pgp)^S$ can be independently a thiol protecting group or H; m, n and p are each an integer that is independently 2 or 3; A is linear or cyclic lower alkyl, aryl, heterocyclyl, combinations or substituted derivatives thereof; $R^7$ is $C_1$–$C_4$ alkyl; and X is a covalent linkage to $L^2$; or

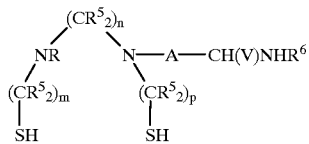
X.

wherein each $R^5$ is independently H, lower alkyl having 1 to 6 carbon atoms, phenyl, or phenyl substituted with lower alkyl or lower alkoxy; m, n and p are each an integer that is independently 1 or 2; A is linear or cyclic lower alkyl, aryl, heterocyclyl, combinations or substituted derivatives thereof; V is H or carbonyl covalently linked to $L^2$, $R^6$ is H or a covalent linkage to $L^2$, and $R^7$ is $C_1$–$C_4$ alkyl, provided that when V is H, $R^6$ is a covalent linkage to $L^2$ and when $R^6$ is H, V is a carbonyl covalenily linked to $L^2$; and a diamino dioxime having the formula:

$$HON=CR^8CR^8{}_2NH(CR^8{}_2)_3NHCR^8{}_2CR^8=NOH$$

where each $R^8$ is independently H, $C_1$ to $C_4$ alkyl, or aryl and one $R^8$ is covalently linked to $L^2$; and a bis-thiosemicarbazone which has a formula:

$$H_2NC(S)NHN=CR(CR_2)_nCR=NNHC(S)NH_2$$

where n is an integer that is 0 or 1 and where each R is independently H, $C_1$ to $C_4$ alkyl, or aryl and one R is covalently linked to $L^2$; and diethylenetriaminepentaacetic acid (DTPA)

$$(HOOCCH_2)_2N(CR_2)(CR_2)N(CH_2COOH)(CR_2)(CR_2)N(CH_2COOH)_2$$

or ethylenediarninetetraacetic acid (EDTA)

$$(HOOCCH_2)_2N(CR_2)(CR_2)N(CH_2COOH)_2$$

where each R is independently H, $C_1$ to $C_4$ alkyl, or aryl and one R is covalently linked to $L^1$; and 1,4,7,10-tetraazadodecanetetraacetic acid

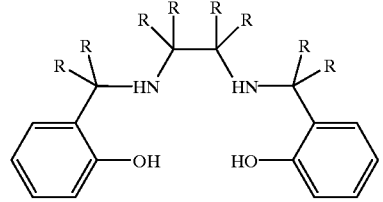

R=H or lower alkyl and one R is a covalent linkage to $L^1$;

or

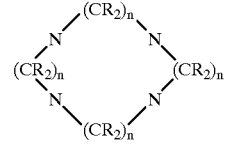

where n is an integer that is 2 or 3, and each R is independently H, $C_1$ to $C_4$ alky, or aryl, and one R is covalently linked to $L^2$; and desferrioxamine.

In one embodiment, the invention provides a reagent of formula (II) wherein the group Z is selected from the group consisting of:

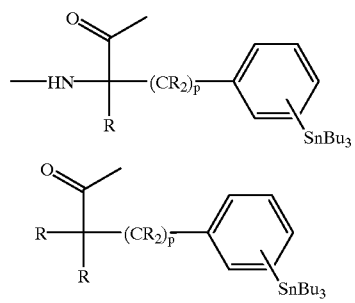

In another embodiment, the invention provides a reagent of formula (II) wherein the group Z comprises the peptide sequence (Gly-Gly-Cys-).

In another embodiment, the invention provides a reagent of formula (II) wherein the group Z comprises the peptide sequence (-Cys(Acm)-Gly-Cys(Acm)-).

In another embodiment, the invention provides a reagent of formula (II) wherein the group Z comprises the peptide sequence (-ε-Lys)-Gly-Cys-).

The term amino acid as used in this invention is intended to include all L- and D- primary α- or β-amino acids, naturally occurring, modified, substituted, altered and otherwise. Specific-binding compounds provided by the invention include but are not limited to compounds of the formula:

[29]
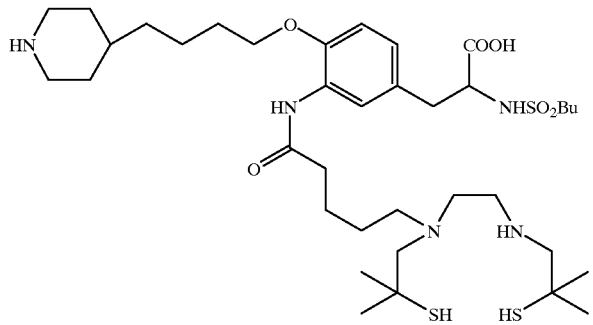

[32]
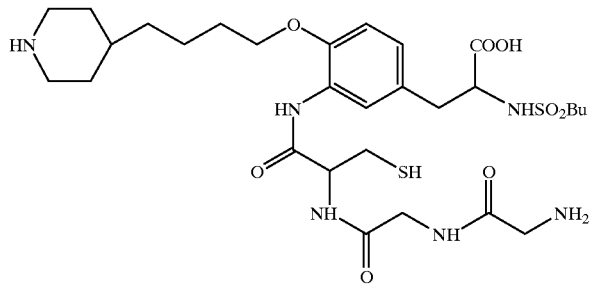

[6]
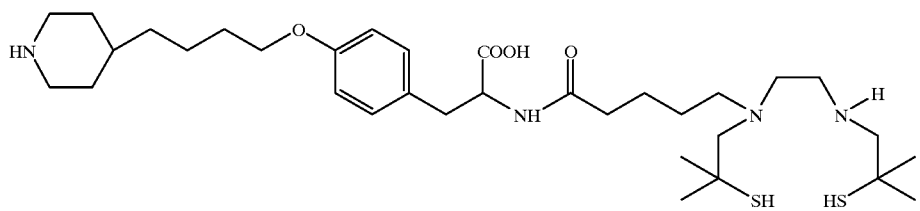

[10]
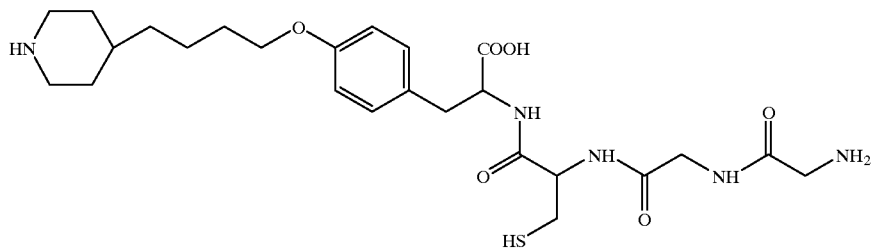

[14]
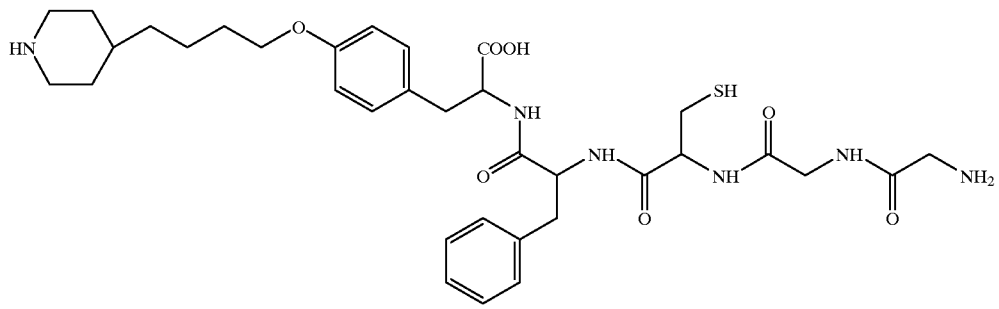

-continued

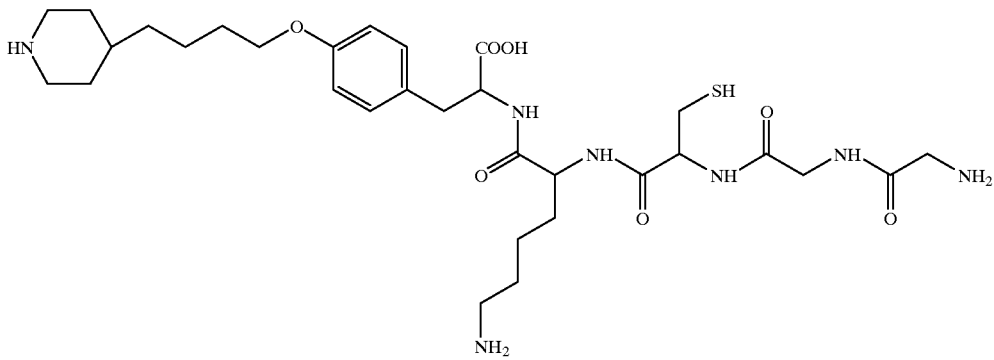

[18]

In forming scintigraphic imaging imaging agents which are complexes of radioactive technetium with the reagents of this invention, technetium-99m, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand. This process is known as ligand exchange and is well known to those skilled in the art. In non-limiting examples, the labile complex may be formed using such transfer ligands as tartrate, citrate, gluconate or mannitol, for example. Exemplary Tc-99m pertechnetate salts useful with the present invention include, for example, alkali metal salts such as the sodium salt, or ammonium salts or lower alkyl ammonium salts.

In a preferred embodiment of the invention, a kit for preparing Tc-99m-labeled compounds is provided. An appropriate amount of a reagent of the invention is provided in a vial that also contains a reducing agent, such as stannous chloride, in an amount sufficient to label the reagent with Tc-99m. An appropriate amount of a transfer ligand as described (such as tartrate, citrate, gluconate or mannitol, for example) can also be included. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form.

Radiolabeled thrombus scintigraphic imaging reagents according to the present invention may be prepared using such a kit by the addition of an appropriate amount of Tc-99m or Tc-99m complex into the vials provided and reacted under conditions as described in Example 4 below.

Scintigraphic thrombus imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

The scintigraphic thrombus imaging reagents provided by the present invention can be used for visualizing thrombi in a mammalian body when radiolabeled, preferably with Tc-99m. In accordance with this invention, the Tc-99m labeled reagents are administered in a single unit injectable dose. The Tc-99m labeled reagents provided by the invention may be administered intravenously in any conventional medium for intravenous injection such as an aqueous saline medium, or in blood plasma medium. Generally, the unit dose to be administered has an amount of radioactivity from about 0.01 mCi to about 100 mCi, preferably 1 mCi to 20 mCi. The solution to be injected at unit dosage is from about 0.01 mL to about 10 mL. After intravenous administration, imaging of the thrombus in vivo can take place in a matter of a few minutes. However, imaging can take place, if desired, in hours or even longer, after the scintigraphic imaging agent is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Synthesis of N-[$N^6$,$N^9$-bis(2-mercapto-2-methylpropyl)-6,9-diazanonanoyl]-3-{4-[4-(piperidin-4-yl)butoxy]phenyl}alanine (Scheme 1, Compound [6])

Compound [2]: N-benzyloxycarbonyl-3-{4-[4-(N-t-butoxycarbonyl piperidin-4-yl)butoxy]phenyl}alanine, t-butyl ester A solution of N-benzyloxycarbonyl-3-{4-[4-(N-t-butoxycarbonyl piperidin-4-yl)butoxy]phenyl}alanine (Compound [1]) (511 mg, 1.0 mmol) in 100 mL methylene chloride is mixed with O-t-butyl-N,N'-diisopropyl isourea (282 mg, 1.5 mmol) and then refluxed for 12 hours, cooled at 4° C. and filtered. The resulting filtrate is evaporated and the concentrated product chromatographed in silica gel (using a chloroform/ethanol solvent system) to give the title compound [2].

Compound [3]: 3-{4-[4-(N-t-butoxycarbonyl-piperidin-4-yl)butoxy]phenyl}alanine, t-butyl ester N-benzyloxycarbonyl-3-{4-[4-(N-t-butoxycarbonyl-piperidin-4-yl)butoxy]phenyl}alanine, t-butyl ester (567 mg, 1.0 mmol) as prepared above is dissolved in 50 mL ethyl acetate. 500 mg palladium on carbon (Pd/C, 10%) catalyst is added, and the mixture is then placed under $H_2$ (30 p.s.i.) for 24 hours. After the reaction is complete, the mixture is filtered through Celite and the filtrate evaporated to give the title compound [3].

Compound [5]: N-[$N^9$-t-butoxycarbonyl-$N^6$,$N^9$-bis(2-triphenylmethylthio-2-methylpropyl)-6,9-diazanonanoyl)]-3-{4-[4-(N-t-butoxycarbonyl piperidin-4-yl)butoxy]phenyl}alanine, t-butyl ester A solution of 3-{4-[4-(N-t-butoxycarbonyl piperidin-4-yl)butoxy]phenyl}alanine, t-butyl ester (433 mg, 1.0 mmol) as prepared above and diisopropyl ethylamine (0.35 mL, 2 mmol) in 5 mL dimethylformamide (DMF) is prepared. To this solution is added $N^9$-t-butoxycarbonyl-$N^6$,$N^9$-bis(2-triphenylmethylthio-2-methylpropyl)-6,9-diazanonanoic acid, N-hydroxysuccinimide ester (Compound [4]) (921 mg, 1 mmol) in 20 mL DMF, prepared from $N^9$-Boc-$N^6$,$N^9$-bis(2-triphenylmethylthio-2-methylpropyl)-6,9-diazanonanoic acid and diisopropylcarbodiimide (DIC)/N-hydroxysuccinimide (HOSu) in tetrahydrofuran (THF) (as described in co-pending International Patent Application WO93/21962). This mixture is stirred at room temperature for 18 hours, and then the reaction mixture is partitioned between water and ethyl acetate. The organic phase is washed sequentially with 1N $H_3PO_4$, water, 5% $NaHCO_3$ and saturated brine, dried with $MgSO_4$, filtered and evaporated. The residue is then flash chromatographed on a silica gel (using a chloroform/ethanol solvent system) to yield title compound [5].

Compound [6]: N-[$N^6$,$N^9$-bis(2-mercapto-2-methylpropyl)-6,9-diazanonanoyl]-3-{4-[4-(piperidin-4-yl)butoxy]phenyl}alanine N-[$N^9$-t-butoxycarbonyl-$N^6$,$N^9$-bis(2-triphenylmethylthio-2-methylpropyl)-6,9-diazanonanoyl)]-3-{4-[4-(N-t-butoxycarbonyl piperidin-4-yl)butoxy]phenyl}alanine, t-butyl ester is treated with a solution of 90% trifluoroacetic acid, 5% water, 2% triethylsilane and 3% $HSCH_2CH_2SH$ (4 mL per mmol of Compound [5]) for 90 minutes, then evaporated several times with chloroform and then chromatographed on a silica gel (using a chloroform/ethanol solvent system) to yield title compound [5].

EXAMPLE 2

Synthesis of N-[glycyl-glycyl-cysteinyl-3-{4-[4-(piperidin-4-yl)butoxy]phenyl}alanine (Scheme 2, Compound [10])

Compound [7]: Fluorenylmethoxycarbonyl-glycylglycyl-(S-triphenylmethyl) cysteine, N-hydroxysuccinimide ester Fluorenylmethoxycarbonyl-glycylglycyl-(S-triphenylmethyl)cysteine (Compound [33]) is prepared using solid-phase peptide synthesis techniques described in greater detail below. The amino-terminal Fmoc protecting group is left on the peptide, and following cleavage of the peptide from the resin the peptide is retritylated and chromatographically purified to give Compound [23]. Compound [33] is dissolved in a 50:50 mixture of DMF/FHF and is then treated with 1.05 molar equivalents of DIC and HOSu to give a solution of title Compound [7].

Compound [8]: N-[fluorenylmethoxycarbonyl-glycylglycyl-(S-triphenylmethyl)cysteiny]-3-{4-[4-(N-t-butoxycarbonyl piperidin-4-yl)butoxy]phenyl}alanine, t-butyl ester To a solution of 3-{4-[4-(N-t-butoxycarbonyl piperidin-4-yl)butoxy]phenyl}alanine, t-butyl ester (Compound [3]) and diisopropylethylamine (0.35 mL, 2 mmol) in 50 mL DMF is added a solution of 1.1 mmol of the N-hydroxysuccinimide ester of Fmoc-Gly-Gly-Cys(S-triphenylmethyl) in THF/DMF. This solution is stirred for 12 hours, and then partitioned between water and ethylacetate. The organic phase is washed sequentially with 1N $H_3PO_4$, water, 5% $NaHCO_3$ and saturated brine, dried with $MgSO_4$, filtered and evaporated to yield title compound [8].

Compound [9]: N-[glycyl-glycyl-(S-triphenylmethyl)cysteinyl]-3-{4-[4-(N-t-butoxycarbonyl-piperidin-4-yl)butoxy]phenyl}alanine, t-butyl ester Compound [8], prepared as described above, is dissolved in a 50 mL of a 50:50 mixture of diethylamine/THF and stirred for 4 hours at room temperature and then evaporated twice with additional THF to give a crude preparation of the title compound [9].

Compound [10]: N-[glycyl-glycyl-cysteinyl]-3-{4-[4-(N-t-butoxycarbonyl-piperidin4-yl)butoxy]phenyl}alanine The crude preparation of Compound [9], prepared as described above, is treated with a solution of 90% trifluoroacetic acid, 5% water, 2% triethylsilicon hydride and 3% $HSCH_2CH_2SH$ (4 mL per mmol of Compound [9]) for 90 minutes, then evaporated several times with chloroform and then chromatographed by HPLC on a C 18 reverse phase column, using an acetonitrile/water/trifluoroacetic acid solvent system, to yield title compound [10].

EXAMPLE 3

Synthesis of N-[glycyl-glycyl-cysteinyl-phenylalanyl]-3-{4-[4-(piperidin-4-yl)butoxy]phenyl}alanine (Scheme 3, Compound [14])

Compound [11]: Fluorenylmethoxycarbonyl-glycylglycyl-(S-triphenylmethyl) cysteinylphenylalanine, N-hydroxysuccinimide ester Fluorenylmethoxycarbonyl-glycylglycyl-(S-triphenylmethyl)cysteinylphenylalanine (Compound [34]) is prepared using solid-phase peptide synthesis techniques described in greater detail below. The amino-terminal Fmoc protecting group is left on the peptide, and following cleavage of the peptide from the resin the peptide is retritylated and chromatographically purified. Compound [34] is dissolved in a 50:50 mixture of DMF/THF and is then treated with 1.05 molar equivalents of DIC and HOSu to give a solution of title Compound [11].

Compound [12]: N-[fluorenylmethoxycarbonyl-glycylglycyl-(S-triphenylmethyl)cysteinylphenylalanyl]-3-{4-[4-(N-t-butoxycarbonyl piperidin-4-yl)butoxy]phenyl}alanine, t-butyl ester To a solution of 3-{4-[4-(N-t-butoxycarbonyl piperidin-4-yl)butoxy]phenyl}alanine, t-butyl ester (Compound [3]) and diisopropylethylamine (0.35 mL, 2 mmol) in 50 mL DMF is added a solution of 1.1 mmol of the N-hydroxysuccinimide ester of Fmoc-Gly-Gly-Cys(S-triphenylmethyl)-Phe (Compound [11]) in THF/DMF. This solution is stirred for 12 hours, and then partitioned between water and ethylacetate. The organic phase is washed sequentially with 1N $H_3PO_4$, water, 5% $NaHCO_3$ and saturated brine, dried with $MgSO_4$, filtered and evaporated to yield title compound [12].

Compound [13]: N-[glycyl-glycyl-(S-triphenyhnethyl)cysteinyl-phenylalanyl]-3-{4-[4-(N-t-butoxycarbonyl-piperidin-4-yl)butoxy]phenyl}alanine t-butyl ester Compound [12], prepared as described above, is dissolved in a 50 mL of a 50:50 mixture of diethylamine/THF and stirred for 4 hours at room temperature and then evaporated twice with additional THF to give a crude preparation of the title compound [13].

Compound [14]: N-[glycyl-glycyl-cysteinyl-phenylalanyl]-3-{4-[4-(N-t-butoxycarbonyl-piperidin-4-yl)butoxy]phenyl}alanine The crude preparation of Compound [13], prepared as described above, is treated with a solution of 90% trifluoroacetic acid, 5% water, 2% triethylsilicon hydride and 3% $HSCH_2CH_2SH$ (4 mL per mmol of Compound [13]) for 90 minutes, then evaporated several times with chloroform and then chromatographed by HPLC on a C18 reverse phase column, using an acetonitrile/water/trifluoroacetic acid solvent system, to yield title compound [14].

EXAMPLE 4

Synthesis of N-[glycyl-glycyl-cysteinyl-lysyl]-3-{4-[4-(piperidin-4-yl)butoxy]phenyl}alanine (Scheme 4, Compound [18])

Compound [15]: Fluorenylmethoxycarbonyl-glycylglycyl-(S-triphenylmethyl) cysteinyl-(N-ε-t-butoxycarbonyl)lysine, N-hydroxysuccinimide ester Fluorenylmethoxycarbonyl-glycylglycyl-(S-triphenylmethyl)cysteinyl-(N-ε-t-butoxycarbonyl)lysine (Compound [35]) is prepared using solid-phase peptide synthesis techniques described in greater detail below. The amino-terminal Fmoc protecting group is left on the peptide. Following cleavage of the peptide from the resin, the peptide is retritylated, the (N-ε-t-butoxycarbonyl) group is re-introduced using di-t-butylcarbonate and the product chromatographically purified to give Compound [35]. Compound [35] is dissolved in a 50:50 mixture of DMF/THF and is then treated with 1.05 molar equivalents of DIC and HOSu to give a solution of title Compound [15].

Compound [16]: N-[fluorenylmethoxycarbonyl-glycylglycyl-(S-triphenylmethyl)cysteinyl-((N-ε-t-butoxycarbonyl)lysyl]-3-{4-[4-(N-t-butoxycarbonyl piperidin-4-yl)butoxy]phenyl}alanine, t-butyl ester To a solution of 3-{4-[4-(N-t-butoxycarbonyl piperidin-4-yl)butoxy]phenyl}alanine, t-butyl ester (Compound [3]) and diisopropylethylamine (0.35 mL, 2 mmol) in 5 mL DMF is added a solution of 1.1 mmol of the N-hydroxysuccinimide ester of Fmoc-Gly-Gly-Cys(S-triphenylmethyl)-Lys(Boc) in THF/DMF. This solution is stirred for 12 hours, and then partitioned between water and ethylacetate. The organic phase is washed sequentially with 1N $H_3PO_4$, water, 5% $NaHCO_3$ and saturated brine, dried with $MgSO_4$, filtered and evaporated to yield title compound [16].

Compound [17]: N-[glycyl-glycyl-(S-triphenylmethyl) cysteinyl-(t-butoxyarbonyl)lysyl]-3-{4-[4-(N-t-butoxycarbonyl-piperidin-4-yl)butoxy]phenyl}alanine, t-butyl ester Compound [16], prepared as described above, is dissolved in a 50 mL of a 50:50 mixture of diethylamine/THF and stirred for 4 hours at room temperature and then evaporated twice with additional THF to give a crude preparation of the title compound [17].

Compound [18]: N-[glycyl-glycyl-cysteinyl-lysyl]-3-{4-[4-(N-t-butoxycarbonyl-piperidin-4-yl)butoxy]phenyl}alanine The crude preparation of Compound [17], prepared as described above, is treated with a solution of 90% trifluoroacetic acid, 5% water, 2% triethylsilicon hydride and 3% $HSCH_2CH_2SH$ (4 mL per mmol of Compound [17]) for 90 minutes, then evaporated several times with chloroform and then chromatographed by HPLC on a C18 reverse phase column, using an acetonitrile/water/trifluoroacetic acid solvent system, to yield title compound [18].

EXAMPLE 5

Preparation of N-[butylsulfonyl)-3-{3-($N^6$,$N^9$-bis(2-mercapto-2-methylpropyl)-6,9-diazanonanamido)-4-[4-(piperidin4-yl)butoxy]phenyl}alanine (Scheme 5, Compound [29])

Compound [20]: 3-(2,2,2-trichloroethyloxycarbonylamino)-tyrosine

The $N^3$-Troc derivative of 3-aminotyrosine (Compound [19]) (supplied by Aldrich Chemical Co., Milwaukee, Wis. as the dihydrochloride hydrate) is prepared using TrocCl and the copper (II) complex of 3-aminotyrosine essentially as reported for the preparation of ε-Tos-lysine in Bodansky et al. (1984, *The Practice of Peptide Synthesis*, Springer-Verlag: New York).

Compound [21]: N-benzyloxycarbonyl-3-(2,2,2-trichloroethyloxycarbonylamino)-tyrosine Compound [20] (36 g, 100 mmol), prepared as described above, is dissolved in 2M NaOH and cooled in an ice bath. To this solution is then added 18.7 g (110 mmol) of phenyl-$CH_2OCOCl$ in a manner such that the temperature of the mixture does not exceed 5° C. 30 minutes after the addition of phenyl-$CH_2OCOCl$ is complete, the solution is washed with ether and the pH of the aqueous fraction adjusted to pH 4 by the addition of an appropriate amount of 1M citric acid. Title compound [21] is then recovered by filtration of this mixture.

Compound [23]: N-benzyloxycarbonyl-3-{3-(2,2,2-trichloroethyloxycarbonyl amino)-4-[4-(N-t-butoxycarbonyl-piperidin-4-yl)butoxy]phenyl}alanine A solution of Compound [21] (5.06 g, 10 mmol), prepared as described above, and cooled in a ice bath is treated with a suspension of sodium hydride (0.48 g, 20 mmol) in 10 mL of DMF. After incubating this mixture at a temperature of less than 10° C. for 60 minutes, 4-(N-t-butoxycarbonyl-piperidin-4-yl)butyl bromide (Compound [22]) (2.76 g, 10 mmol) is added in 30 mL DMF. The reaction is allowed to proceed at room temperature overnight, and then the product is concentrated, diluted with ethyl acetate, and then washed sequentially with 1N $H_3PO_4$, water, and saturated brine, dried with $MgSO_4$, filtered, evaporated and chromatographed on a silica gel (using a chloroform/ethanol solvent system) to yield title compound [23].

Compound [24]: N-benzyloxycarbonyl-3-{3-(2,2,2-trichloroethylolycarbonyl amino)-4-[4-(N-t-butoxycarbonyl-piperidin-4-yl)butoxy]phenyl}alanine, t-butyl ester Compound [23] (782 mg, 1 mmol), prepared as described above, is dissolved in 50 mL methylene chloride and treated with O-t-butyl-N,N'-diisopropylisourea (282 mg, 1.5 mmol) at reflux for 12 hours, cooled at 4° C. and filtered. The resulting filtrate is evaporated and the concentrated product chromatographed in silica gel (using a chloroform/ethanol solvent system) to give the title compound [24].

Compound [26]: N-(butylsulfonyl)-3-{3-(2,2,2-trichloroethyloxycarbonylamino)4-[4-(N-t-butoxycarbonyi-piperidin4-yl)butoxy]phenyl}alanine-butyl ester Compound [24] is hydrogenated as described above for Compound [2] to yield 3-{3-(2,2,2-trichloroethyloxycarbonyl amino)-4-[4-(N-t-butoxycarbonyl-piperidin-4-yl)butoxy] phenyl}alanine, t-butyl ester (Compound [25]). Compound [25] is then dissolved in THF containing 1 molar equivalent of diisopropylethylamine and treated with 1 molar equivalent of n-butylsulfonylchloride. The resulting mixture is evaporated, re-dissolved in ethylacetate, washed sequentially with 5% $NaHCO_3$, water, and saturated brine, dried using $MgSO_4$, filtered, evaporated and chromatographed on a silica gel (using a chloroform/ethanol solvent system) to yield title compound [26].

Compound [27]: N-(butylsulfonyl)-3-{3-amino)-4-[4-(N-t-butoxycarbonyl-piperidin-4-yl)butoxy]phenyl}alanine, t-butyl ester To a solution of Compound [26] (860 mg, 1 mmol) dissolved in 50 mL THF containing 1 mL acetic acid is added 0.5 g zinc metal, and the mixture is stirred at room temperature for 12 hours. The reaction mixture is then evaporated, re-dissolved in ethyl acetate, and washed sequentially with 1N HCl, water, 5% $NaHCO_3$, and saturated saline, dried with $MgSO_4$, filtered and evaporated to give title compound [27], which is then purified by chromatography on a silica gel (using a chloroform/ethanol solvent system).

Compound [28]: N-(butylsulfonyl)-3-{3-($N^9$-t-butoxycarbonyl-$N^6$,$N^9$-bis(2-methyl-2-triphenylmethylthiopropyl)-6,9-diazanonanamido)-4-[4-(N-t-butoxycarbonyl-piperidin-4-yl)butoxy]phenyl}alanine, t-butyl ester To a solution of Compound [27] (685 mg, 1 mmol) dissolved in 50 mL of a 50:50 mixture of DMF/THF containing diisopropylethylamine (0.35 mL, 2 mmol) is added a solution of $N^9$-t-butoxycarbonyl-$N^6$,$N^9$-bis(2-triphenylmethylthio-2-methylpropyl)-6,9-diazanonanoic acid, N-hydroxysuccinimide ester (Compound [4]) (921 mg, 1 mmol) in 10 mL DMF. After reaction for 4 hours at room temperature, the reaction mixture was evaporated, re-dissolved in ethylacetate, washed sequentially with 1N $H_3PO_4$, water, and saturated brine, dried with $MgSO_4$, filtered and evaporated to yield title compound [28].

Compound [29]: N-(butylsulfonyl)-3-{3-($N^6$,$N^9$-bis(2-mercapto-2-methylpropyl)-6,9-diazanonanamido)-4-[4-(piperidin-4-yl)butoxy]phenyl}alanine Compound [28], prepared as described above, is deprotected as described above for Compound [5] to yield title Compound [29], which is then purified by reverse-phase HPLC using, using an acetonitrile/water/trifluoroacetic acid solvent system.

EXAMPLE 6

Preparation of 3-(glycyl-glycyl-cysteinamido)-N-α-n-butylsulfonyl-tyrosine (Scheme 6, Compound [30])

Compound [30]: N(butylsulfonyl)-3-{3-(fluorenylmethoxycarbonyl-glycylglycyl-(S-triphenylmethyl)cysteinylamino)-4-[4-(N-t-butoxycarbonyl-piperidin-4-yl)butoxy]phenyl}alanine, t-butyl ester To a solution of Compound [27] (685 mg, 1 mmol), prepared as described above, dissolved in 50 mL DMF containing 0.35 mL (2 mmol) diisopropylethylamine, is added a solution of Fmoc (fluorenylmethoxycarbonyl)-Gly-Gly-Cys(S-triphenylmethyl)-N-hydroxysuccinamide ester (Compound [7]) (1.1 mmol) in 10 mL DMF. After reaction for 4 hours at room temperature, the reaction mixture is partitioned between water and ethyl acetate. The organic phase is washed sequentially with 1N $H_3PO_4$, water, 5% $NaHCO_3$ and saturated brine, dried with $MgSO_4$, filtered and evaporated. The residue is then flash chromatographed on a silica gel (using a chloroform/ethanol solvent system) to yield title compound [30].

Compound [32]: 3-(glycyl-glycyl-cysteinamido)-N-α-n-butylsulfonyl-tyrosine

Compound [30], prepared as described above, is deprotected as described above for Compound [8] to yield title Compound [32], which is then purified by reverse-phase HPLC using, using an acetonitrile/water/trifluoroacetic acid solvent system.

EXAMPLE 7

Synthesis of BAT Chelators

A. Synthesis of $N^9$-(t-butoxycarbonyl)-$N^6$,$N^9$-bis(2-methyl-2-triphenylmethylthiopropyl)-6,9-diazanonanoic acid a. 2-methyl-2-(triphenylmethylthio)propanal Triphenylmethylmercaptan (362.94 g, 1.31 mol, 100 mol %) dissolved in anhydrous THF (2 L) was cooled in an ice bath under argon. Sodium hydride (60% in oil; 54.39 g, 1.35 mol, 104 mol %) was added in portions over 20 min. 2-bromo-2-methylpropanal (206.06 g, 1.36 mol, 104 mol %; see Stevens & Gillis, 1957, J. Amer. Chem. Soc. 79: 3448–51) was then added slowly over 20 min. The reaction mixture was allowed to warm to room temperature and stirred for 12 hours. The reaction was quenched with water (1 L) and extracted with diethyl ether (3×1 L). The ether extracts were combined, washed with saturated NaCl solution (500 mL), dried over $Na_2SO_4$ and filtered. The solvent was removed under reduced pressure to afford a thick orange oil. The crude oil was dissolved in toluene (200 mL) and diluted to 2 L with hot hexanes. The mixture was filtered through a sintered glass funnel and cooled at −5° C. for 12 hours. The white crystalline solid which formed was removed by filtration to afford 266.36 g (59% yield) of the title compound. The melting point of the resulting compound was determined to be 83–85° C. Nuclear magnetic resonance characterization experiments yielded the following molecular signature:

$^1$H NMR(300 MHz, $CDCl_3$): δ 1.24(s, 6H, $2CH_3$), 7.2–7.35 (m, 9H), 7.59–7.62 (m,6H), 8.69 (s, H, —COH)

$^{13}$C NMR (75 $MH_z$, $CDCl_3$): δ 22.86, 55.66, 67.48, 126.85, 127.75, 129.72, 144.79, 197.31.

b. N,N'-bis(2-methyl-2-triphenylmethylthioropyl) ethylenediamine.

Ethylenediamine (1.3 mL, 0.0194 mol, 100 mol %) was added to 2-methyl-2-(triphenylmethylthio)propanal (13.86 g, 0.0401 mol, 206 mol %) dissolved in methanol (40 mL) and anhydrous THF (40 mL) under argon, and the pH was adjusted to pH 6 by dropwise addition of acetic acid. The solution was stirred for 20 min at 20° C. Sodium cyanoborohydride (1.22 g, 0.0194 mol, 100 mol %) was added and the reaction was stirred at room temperature for 3 hours. Additional sodium cyanoborohydride (1.08 g) was added and the reaction was stirred at 20° C. for 17 hours. A final portion of sodium cyanoborohydride (1.02 g) was added and the reaction heated at reflux under argon for 6 hours. The reaction was quenched with 0.5 M HCl (100 mL) and extracted with ethyl acetate (2×100 mL). The organic extracts were combined, sequentially washed with 2 M NaOH (60 mL), saturated NaCl solution (60 mL), dried ($Na_2SO_4$), and filtered. The solvent was removed under reduced pressure to give 16.67 g of crude product which was crystallized from toluene/hexanes to afford 10.20 g (73% yield) of white crystals of the title compound. The melting point of the resulting compound was determined to be 83–86° C. FABMS analysis yielded an m/z of 721 (MH+). Nuclear magnetic resonance characterization experiments yielded the following molecular signature:

$^1$H NMR (300 $MH_z$, $CDCl_3$): δ1.12 (s, 12H, 4 $CH_3$), 1.64 (s, 4H, N—$CH_2$-$C(Me)_2$-S), 2.52 (s, 4H, N—$CH_2$-$CH_2$-N), 5.31 (S, 2H, 2-NH), 7.12–7.30 (m, 18H, Ar), 7.62–7.65 (m, 12H, Ar).

c. $N^6$,$N^9$-bis(2-methyl-2-triphenylmethylthiopropyl)-6,9-diazanonanoic acid, ethyl ester $K_2CO_3$ (1.92 g, 13.9 mmol, 100 mol %) was added to N,N'-bis(2-methyl-2-triphenylmethylthioropyl)

ethylenediamine (10.03 g, 13.9 mmol) in CH₃CN (60 mL), followed by ethyl 5-bromovalerate (3.30 mL, 20.8 mmol, 150 mol %). The reaction was heated at reflux under argon overnight. The solution was then concentrated to a paste and partitioned between 0.25 M KOH (100 mL) and ethyl acetate (100 mL). The aqueous layer was extracted with ethyl acetate (1×50 mL) and the combined ethyl acetate layers were washed with 50 mL water and NaCl solution (2×50 mL), dried with Na₂SO₄ and concentrated to an orange oil. Purification by flash chromatography (300 g flash silica, 100% CHCl₃ to 5% MeOH/CHCl₃) gave pure title compound (7.75 g, 66% yield). FABMS analysis yielded an (MH+) of 849 (compared with a calculated molecular weight of 849.24 for the compound $C_{55}H_{64}N_2O_2S_2$).

d. $N^9$-(t-butoxycarbonyl)-$N^6$,$N^9$-bis(2-methyl-2-triphenylmethylthiopropyl)-6,9-diazanonanoic acid 1M KOH (25 mL, 25.0 mmol, 274 mol %) was added to $N^6$,$N^9$-bis(2-methyl-2-triphenylmethylthiopropyl)-6,9-diazanonanoic acid, ethyl ester (7.75 g, 9.13 mmol) in dioxane (200 mL), followed by water (250 mL). Dioxane was then added dropwise with stirring until a homogeneous solution was obtained. The reaction was heated at a slow reflux overnight. Most of the dioxane was removed by rotary evaporation and the pH of solution was adjusted to ~7-8 with 1 M KH₂PO₄ and saturated NaHCO₃. The solution was then extracted with ethyl acetate (3×75 mL) and the combined organic layers were washed with NaCl solution (50 mL), dried with Na₂SO₄ and concentrated to a foam/solid (6.35 g, 85% yield).

To the crude product from the above reaction was added (BOC)₂O (3.35 g, 15.4 mmol, 200 mol %), CH₃CN (50 mL) and methylene chloride (50 mL), followed by triethylamine (1.0 mL, 7.2 mmol, 93 mol %). The reaction was stirred at room temperature under argon overnight. The reaction solution was then concentrated and partitioned between water (100 mL) and ethyl acetate (50 mL). The aqueous layer was extracted with ethyl acetate (1×50 mL) and the combined ethyl acetate layers were washed with 5% citric acid and NaCl solution (50 mL each), then dried (Na₂SO₄) and concentrated to an orange oil. Purification by flash chromatography (200 g flash silica, 100% CDCl₃ to 5% methanol/chloroform) gave pure title compound (2.58 g. 36% yield). FABMS analysis gave an (MH+) of 921 (compared with the calculated value of 921.31 for the compound $C_{58}H_{68}N_2O_4S_2$).

B. Synthesis of $N^9$-(t-butoxycarbonyl)-$N^6$,$N^9$-bis(2-methyl-2-(4-methoxybenzylthio)-2-methylpropyl)-6,9-diazanonanoic acid a. N,N'-bis-[2-(4-methoxybenzylthio)-2-methylpropyl]-ethylenediamine A solution of N,N'-bis(2-mercapto-2-methylpropyl) ethylenediamine (11.23 g, 47.5 mmol; see, DiZio et al., 1991, Bioconjugate Chem 2: 353 and Corbin et al., 1976, J. Org. Chem. 41: 489) in methanol (500 mL) was cooled in ice/water bath and then saturated with gaseous ammonia over 45 min. To this was added 4-methoxybenzyl chloride (17.0 mL, 125 mmol, 264 mol %). The reaction was allowed to warm to room temperature overnight with stirring under argon. The solution was concentrated to a paste and then partitioned between diethyl ether (150 mL) and 0.5 M KOH (200 mL). The aqueous layer was further extracted with diethyl ether (2×50 mL). The combined organic layers were washed with NaCl solution and concentrated to a clear colorless oil. The oil dissolved in diethyl ether (200 mL) and then acidified with 4.0 M HCl in dioxane until no further precipitation was seen. The white precipitate was collected by filtration and washed with diethyl ether. The white solid was recrystallized from hot water at a pH of ~2. The product was collected by filtration to afford 29.94 g as a mix of mono- and di-HCl salts. The HCl salts were partitioned between 1 M KOH (100 mL) and ethyl acetate (100 nmL). The aqueous was extracted with ethyl acetate (2×30 mL) and the combined organic layers were washed with NaCl solution, dried with Na₂SO₄ and concentrated to give pure product as the free base as a light yellow oil (18.53 g, 82% yield). Nuclear magnetic resonance characterization experiments yielded the following molecular signature:

¹H NMR (300 MHz, CDCL₃): δ 7.25 (d, 4H, J=9), 6.83 (d, 4H, J=9), 3.78 (s, 6H), 3.67 (s, 4H), 2.63 (s, 4H), 2.56 (s, 4H), 1.34 (s, 12H).

b. N-(5-carboethoxypentyl)-$N^6$,$N^9$-bis-[2-(4-methoxybenzylthio)-2-methylpropyl]-6,9-diazanonanoic acid To N,N'-bis-[2-(4-methoxybenzylthio)-2-methylpropyl]-ethylenediamine (4.13 g, 8.66 mmol) in CH₃CN (50 mL) was added K₂CO₃ (1.21 g, 8.75 mmol, 101 mol %) followed by ethyl 5-bromovalerate (2.80 mL, 17.7 mmol, 204 mol %). The reaction was stirred at reflux overnight and was then concentrated to a paste in vacuo. The residue was partitioned between ethyl acetate (100 mL) and 0.5 M KOH (100 mL). The aqueous layer was extracted with ethyl acetate (1×50 mL) and the combined organic layers were washed with NaCl solution (50 mL), dried with Na₂SO₄ and concentrated to a yellow oil (~6 g). Purification by normal-phase preparative HPLC (100% CHCl₃ to 5% methanol/chloroform over 25 min.) afforded pure title compound (1.759 g, 34% yield). FABMS analysis gave an (MH+) of 605 (compared with the value of 604.90 calculated for $C_{33}H_{52}N_2O_4S_2$). Nuclear magnetic resonance characterization experiments yielded the following molecular signature:

¹H NMR (300 mH₂, CDCl₃): δ 7.25 (d, 4H, J=8.5), 6.83 (d, 4H, J=8.5), 4.13 (q, 2H, J=7), 3.793 (s, 3H), 3.789 (s. 3H), 3.74 (s, 2H), 3.67 (s, 2H), 2.6 (m, 10H), 2.31 (t, 2H, J=7), 1.6 (m, 2H), 1.5 (m 2H), 1.34 (s 12H), 1.28 (t, 3H, J=7).

c. $N^9$-(t-butoxycarbonyl)-$N^6$,$N^9$-bis(2-methyl-2-(4-methoxybenzylthio)-2-methylpropyl)-6,9-diazanonanoic acid To a solution of N-(5-carboethoxypentyl)-$N^6$,$N^9$-bis-[2-(4-methoxybenzylthio)-2-methylpropyl]-6,9-diazanonanoic acid (586 mg, 0.969 mmol) in THF (40 mL) was added water (30 mL) and 1 M KOH (2.5 mL, 2.5 mmol, 260 mol %). The homogeneous solution was heated to a slow reflux overnight. The solution was then cooled to room temperature and the THF was removed under rotary evaporation. The residue was diluted to 50 mL with H₂O and the pH was adjusted to ~2-3 with 1 M HCl. The solution was extracted with ethyl acetate (3×30 mL) and the combined organic layers were washed with NaCl solution (50 mL), dried with NaSO₄ and concentrated to give crude acid (422 mg, 75% yield).

To the crude product from the above reaction was added CH₃CN (40 mL) and (BOC)₂O (240 mg, 1.10 mmol, 150 mol %) followed by triethylamine (0.200 mL, 1.43 mmol, 196 mol %). The homogenous solution stirred at room temperature overnight under argon. The solution was then concentrated to a paste and partitioned between ethyl acetate (25 mL) and 1 M KH₂PO₄ (25 mL). The organic layer was washed with 5% citric acid (2×25 mL) and NaCl solution (25 mL), dried with Na₂SO₄ and concentrated to a yellow oil. Purification by flash chromatography (50 mL flash silica gel, 100% chloroform to 15% methanol/chloroform) gave pure title compound (344 mg, 70% yield). FABMS analysis gave an (MH+) of 677 (compared to the value of 676.97 calculated for the compound $C_{36}H_{56}N_2O_6S_2$). Nuclear magnetic resonance characterization experiments yielded the following molecular signature:

$^1$H NMR (300 MHz, CDCl$_3$): δ 7.20 (d, 4H, J=7), 6.79 (d, 4H, J=7), 3.75 (S, 3H), 3.74 (S, 3H), 3.68 (M, 4H), 3.35 (M, 4H), 2.65 (M, 2H), 2.53 (M, 4H), 2.31 (M, 2H), 1.59 (M, 2H), 1.43 (S, 11H), 1.30 (S, 6H), 1.26 (S, 6H)

C. Synthesis of BAM(N$^1$-(t-butoxycarbonyl)-N$^1$,N$^4$-bis[2-methyl-2-(triphenylmethylthio) propyl]-1,4,10-triazadecane A 250 mL single-necked round-bottomed flask, equipped with a stir bar, reflux condenser and argon balloon, was charged with N$^1$,N$^4$-bis[2-methyl-2-(triphenylmethylthio) propyl]-ethylenediamine (BAT-I; 10.0 g, 14.01 mmol) in 50 mL of CH$_3$CN and 30 mL dioxane. To this was added N-(5-bromopentyl)-phthalimide (8.04 g, 27.1 mmol, 194 mole %) followed by K$_2$CO$_3$ (2.95 g, 21.3 mmol, 152 mole %). The mixture was heated at reflux under argon for two days. The reaction mixture was then concentrated and the residue partitioned between 150 mL water and 150 mL ethyl acetate. The organic layer was separated and the aqueous layer (at pH of about 10) was fiurther extracted with 50 mL ethyl acetate. The combined organic layers were washed once with brine (75 mL), dried over Na$_2$CO$_3$ and concentrated to an oil. Purification by low-pressure liquid chromatography (300 g SiO$_2$, CHCl$_3$->2% methanol in CHCl$_3$) afforded 9.20 g of 9-phthalimido-N$^1$,N$^4$-bis[2-methyl-2-(triphenylmethylthio)propyl]-1,4-diazanonane as a yellow foam (70% yield). Chemical analysis of the purified product of this intermediate confirmed its identity as follows:

$^1$H NMR (300 MHz, CDCl$_3$): δ 1.01 (6H,s), 1.03 (6H,s), 1.15–1.4 (2H,t), 1.98 (2H,s), 2.10 (2H,s), 2.28 (2H,m), 2.45 (3H,m), 3.68 (2H,t), 7.15–7.35 (18H, m), 7.62 (12H, t), 7.72 (2H, m), 7.85 (2H,m). FABMS MH$^+$ was predicted to be 935.4 and found to be 936.

A 500 mL single-necked round-bottomed flask, equipped with stir bar, was charged with 9-phthalimido-N$^1$,N$^4$-bis[2-methyl-2-(triphenylmethylthio)propyl]-1,4-diazanonane (8.83 g, 9.43 mmol) in 75 mL of CH$_3$CN and 20 mL CH$_2$Cl$_2$. To this was added K$_2$CO$_3$ (1.30 g, 9,41 mmol, 100 mole %), followed by di-tert-butyl dicarbonate (2.15 g, 9.85 mmol, 104 mole %), and the reaction stirred at room temperature overnight. The reaction mixture was then concentrated and partitioned between 100 mL each of water and ethyl acetate. The organic layer was separated and the aqueous layer was further extracted with 50 mL ethyl acetate. The combined organic layers were washed once with brine (75 mL), dried over Na$_2$SO$_4$ and concentrated to give 9.69 g of crude 9-phthalimido-N$^1$-(t-butoxycarbonyl)-N$^1$,N$^4$-bis[2-methyl-2-(triphenylmethylthio)propyl]- 1,4-diazanonane as a yellow foam (99% crude yield). This crude product was used without further purification.

A 250 mL single-necked round-bottomed flask, equipped with stir bar and reflux condenser, was charged with 9-phthalimido-N-(t-butoxycarbonyl)-N$^1$,N$^4$-bis[2-methyl-2-(triphenylmethylthio)propyl]-1,4-diazanonane (5.50 g, 5.319.43 mmol) in 25 mL of THF. To this was added 100 mL ethanol and 5 mL water. The addition of water caused the starting material to precipitate out of solution. Hydrazine hydrate (1.2 mL, 24.7 mmol, 466 mole %) was added, and the reaction heated at reflux for two days. The reaction mixture was concentrated and partitioned between 100 mL each of water and 0.25M K$_2$CO$_3$. The organic layer was separated and washed once with brine (75 mL), dried over Na$_2$SO$_4$ and concentrated to a solid foam. Purification of the crude product by low-pressure liquid chromatography (100 g SiO$_2$, CHCl$_3$->5% methanol in CHCl$_3$, the column pre-treated with 200 mL 2% triethylamine in CHCl$_3$) afforded 3.27 g of pure N$^1$-(t-butoxycarbonyl)-N$^1$,N$^4$-bis[2-methyl-2-(triphenylmethylthio)propyl]-1,4,10-triazadecane as a yellow foam (68% yield). Chemical analysis of the purified product confirmed its identity as follows:

$^1$H NMR (300 MHz, CDCl$_3$): δ 0.9 (12H,s), 1.2 (6Hs), 1.36 (9H,s), 2.05 (4H,m), 2.24 (2H,t), 2.31 (2H,t), 2.62 (3H,t), 3.0 (2H,s,broad), 3.1 (2H,s,broad), 7.2 (18H,m), 7.6 (12H, t). FABMS MH$^+$ was predicted to be 905.5 and found to be 906.5.

EXAMPLE 8

Synthesis of [BAT]-conjugated(εN)Lys(αN-Fmoc): [N-ε-(N$^9$-t-butoxycarbonyl)-N$^6$,N$^9$-bis[2-methyl-2-(triphenylmethylthio)propyl]-6,9-diazanonanoyl)-N-α-Fmoc-Lysine A 100 mL single-necked round-bottomed flask, equipped with stir bar and argon balloon, was charged with N$^9$-(t-butoxycarbonyl)-N$^6$,N$^9$-bis[2-methyl-2-(triphenylmethylthio)propyl]-6,9-diazanonanoic acid (BAT acid; 3.29 g, 3.57 mmol) in 50 mL CH$_2$Cl$_2$ at room temperature. To this was added diisopropylcarbodiimide (580 μL, 3.70 mmol, 104 mole %) followed immediately by N-hydroxysuccinimide (432 mg, 3.75 mmol, 105 mole %). The reaction was stirred overnight at room temperature during which time a white precipitate developed. The mixture was filtered and the filtrate concentrated to a solid foam. The crude foam, in a 100 mL round-bottomed flask, was dissolved in 75 mL of a 2:1 mixture of dimethoxyethane and water. To this homogeneous solution was added N-α-Fmoc-lysine hydrochloride (1.52 g, 3.75 mmol, 105 mole %) followed by K$_2$CO$_3$ (517 mg, 3.74 mmol, 105 mole %), and the yellow solution stirred overnight at room temperature. The solution was then poured into a 250 mL erlenmeyer flask containing 100 mL of ethyl acetate and 100 mL of water. The organic layer was separated and the aqueous layer further extracted with 50 mL ethyl acetate. The combined organic layers were washed once with brine (100 mL), dried over Na$_2$SO$_4$ and concentrated to a yellow solid. This crude product was purified by low-pressure liquid chromatography (150 g SiO$_2$, eluted with CHCl$_3$ →10% methanol in CHCl$_3$). In this way, 3.12 g of the named compound was prepared (69% yield). Chemical analysis of the purified product confirmed its identity as follows:

$^1$H NMR (300 MHz, CDCl$_3$): δ 0.88 (12H,s,broad), 1.05–1.45 (19H,m), 1.8–2.1 (4H,m), 1.8–2.47 (4H,m), 2.75–3.2 (6H,m), 3.9–4.3 (4H,m,), 7.2 (22H,m), 7.6 (16H, s,bound). FABMS MH$^+$ was predicted to be 1270.6 and found to be 1272.

EXAMPLE 9

Solid Phase Peptide Synthesis

Radiolabel-binding moieties that are or comprise peptide sequences, such as glycyl-glycyl-cysteine, glycyl-glycyl-cysteinyl-phenylalanine, and glycyl-glycyl-cysteinyl-lysine, are prepared by solid phase peptide synthesis (SPPS) which is carried out on a 0.25 millimole (mmole) scale using an Applied Biosystems Model 431A Peptide Synthesizer and using 9-fluorenyl-methyloxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluorophosphate/hydroxy-benzotriazole (HBTU/HOBT), and using p-hydroxymethyl-phenoxymethylpolystyrene (HMP) resin for carboxyl-terminus acids or Rink amide resin for carboxyl-terminus amides.

Where appropriate, 2-chloroacetyl and 2-bromoacetyl groups are introduced either by using the appropriate 2-haloacetic acid as the last residue to be coupled during SPPS or by treating the N-terminus free amino peptide bound to the resin with either the 2-halo-acetic acid/diisopropylcarbodiimide/N-hydroxysuccinimide in NMP of the 2-halo-acetic anhydride/diisopropylethylamine in NMP.

Resin-bound products are routinely cleaved using a solution of trifluoroacetic acid or trifluoroacetic acid/dichloromethane, optionally containing 5% water for 0.5–3 hours at room temperature.

Where appropriate, products were re-S-tritylated in triphenylmethanol/TFA and N-Boc groups were re-introduced using $(Boc)_2O$.

Crude peptides are purified by preparative high pressure liquid chromatography (HPLC) using a Waters Delta Pak C18 column and gradient elution using 0.1% trifluoroacetic acid (TFA) in water modified with acetonitrile. Acetonitrile is evaporated from the eluted fractions which are then lyophilized. The identity of each product is confirmed by fast atom bombardment mass spectroscopy (FABMS) or electrospray mass spectroscopy (ESMS).

EXAMPLE 10

A General Method for Radiolabeling with Tc-99m 0.1 mg of a reagent prepared according to the methods described in Examples 1–7 is dissolved in 0.1 mL of water, or 50/50 ethanol/water or PBS or 50 mM potassium phosphate pH 5, 6, or 7.4. Tc-99m gluceptate is prepared by reconstituting a Glucoscan vial (E.I. DuPont de Nemours, Inc.) with 1.0 mL of Tc-99m sodium pertechnetate containing up to 200 mCi and is allowed to stand for 15 minutes at room temperature. 25 $\mu$L of Tc-99m gluceptate is then added to the reagent and the reaction allowed to proceed at room temperature or at 100° C. for 15–30 min and then filtered through a 0.2 $\mu$m filter.

The Tc-99m labeled reagent purity is determined by HPLC using the following condition: a Waters Delta Pak RP-18, 5$\mu$, 150 mm×3.9mm analytical column is loaded with each radiolabeled reagent and the reagents are eluted at a solvent flow rate equal to 1 mL/min. Gradient elution is performed beginning with 10% solvent A (0.1% CF3COOH/$H_2O$) to 40% solvent $B_{90}$ (0.1% $CF_3COOH$/90% $CH_3CN$/$H_2O$) over the course of 20 min.

Radioactive components are detected by an in-line radiometric detector linked to an integrating recorder. Tc-99m gluceptate and Tc-99m sodium pertechnetate elute between 1 and 4 minutes under these conditions, whereas the Tc-99m labeled reagents of this invention elute after a much greater amount of time.

EXAMPLE 11

Platelet Aggregation Inhibition Assays

Platelet aggregation studies are performed essentially as described by Zucker (1989, Methods in Enzymol. 169: 117–133). Briefly, platelet aggregation is assayed with or without putative platelet aggregation inhibitory compounds using fresh human platelet-rich plasma, comprising 300,000 platelets per microliter. Platelet aggregation is induced by the addition of a solution of adenosine diphosphate to a final concentration of 10 to 15 micromolar, and the extent of platelet aggregation is monitored using a Bio/Data aggregometer (Bio/Data Corp., Horsham, Pa.). The concentrations of platelet aggregation inhibitory compounds used are varied from 0.1 to 500 $\mu$g/mL. The concentration of inhibitor that reduces the extent of platelet aggregation by 50% (defined as the $IC_{50}$) is determined from plots of inhibitor concentration versus extent of platelet aggregation. An inhibition curve for peptide RGDS is determined for each batch of platelets tested as a positive control.

EXAMPLE 12

In Vivo Imaging of Deep Vein Thrombosis in a Canine Model using Tc-99m Labeled Compound Thrombus Scintigraphic Imaging Agents Mongrel dogs (25–35 lb., fasted overnight) are sedated with a combination of ketamine and aceprozamine intramuscularly and then anesthetized with sodium pentabarbital intravenously. An 18-gauge angiocath is inserted in the distal half of the right femoral vein and an 8 mm Dacron® entwined stainless steel embolization coil (Cook Co., Bloomington Ind.) is placed in the femoral vein at approximately mid-femur in each animal. The catheter is removed, the wound sutured and the placement of the coil documented by X-ray. The animals are then allowed to recover overnight.

One day following coil placement, each animal is re-anesthetized, intravenous saline drips placed in each foreleg and a urinary bladder catheter inserted to collect urine. The animal is placed supine under a gamma camera which is equipped with a low-energy, all purpose collimator and photopeaked for Tc-99m. Images are acquired on a nuclear medicine computer system.

Tc-99m labeled reagent [185–370 mBq (5–10 mCi) Tc-99m and 0.2–0.4 mg reagent] is injected into one foreleg intravenous line at its point of insertion. The second line is maintained for blood collection. Anterior images over the legs are acquired for 500,000 counts or 20 min (whichever was shorter), at approximately 10–20 min, and at approximately 1, 2, 3 and 4 h post-injection. Following the collection of the final image, each animal is deeply anesthetized with pentobarbital. Two blood samples are collected on a cardiac puncture using a heparinized syringe followed by a euthanizing dose of saturated potassium chloride solution administered by intercardiac or bolus intravenous injection. The femoral vein containing the thrombus and samples of thigh muscle are then carefully dissected out. The thrombus is then dissected free of the vessel and placed in a pre-weighed test tube. The thrombus samples are then weighed and counted in a gamma well counter in the Tc-99m channel. Known fractions of the injected doses are counted as well.

Fresh thrombus weight, percent injected dose (%ID)/g in the thrombus and blood obtained just prior to euthanasia and thrombus/blood and thrombus/muscle ratios are determined. Thrombus/background ratios were determined by analysis of the counts/pixel measured in regions-of-interest (ROI) drawn over the thrombus and adjacent muscle from computer-stored images. These results are used to demonstrate thrombus-specific localization of radioactivity and the efficacy of scintigraphic imaging to localize sites of thrombus formation in vivo.

It should be understood that the foregoing disclosure emphasizes certain specific embodiments of the invention and that all modifications or alternatives equivalent thereto are within the spirit and scope of the invention as set forth in the appended claims.

Scheme 1
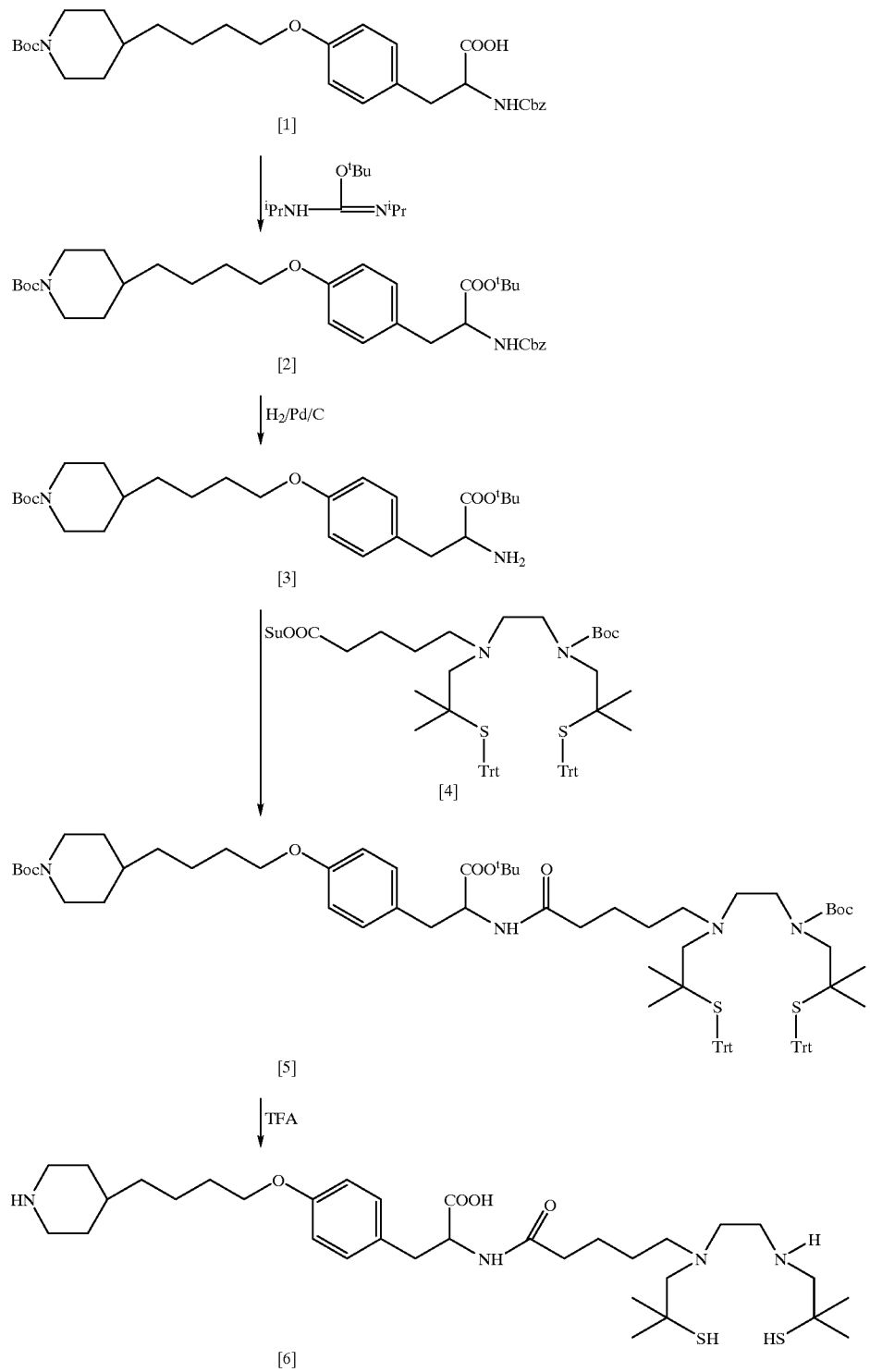

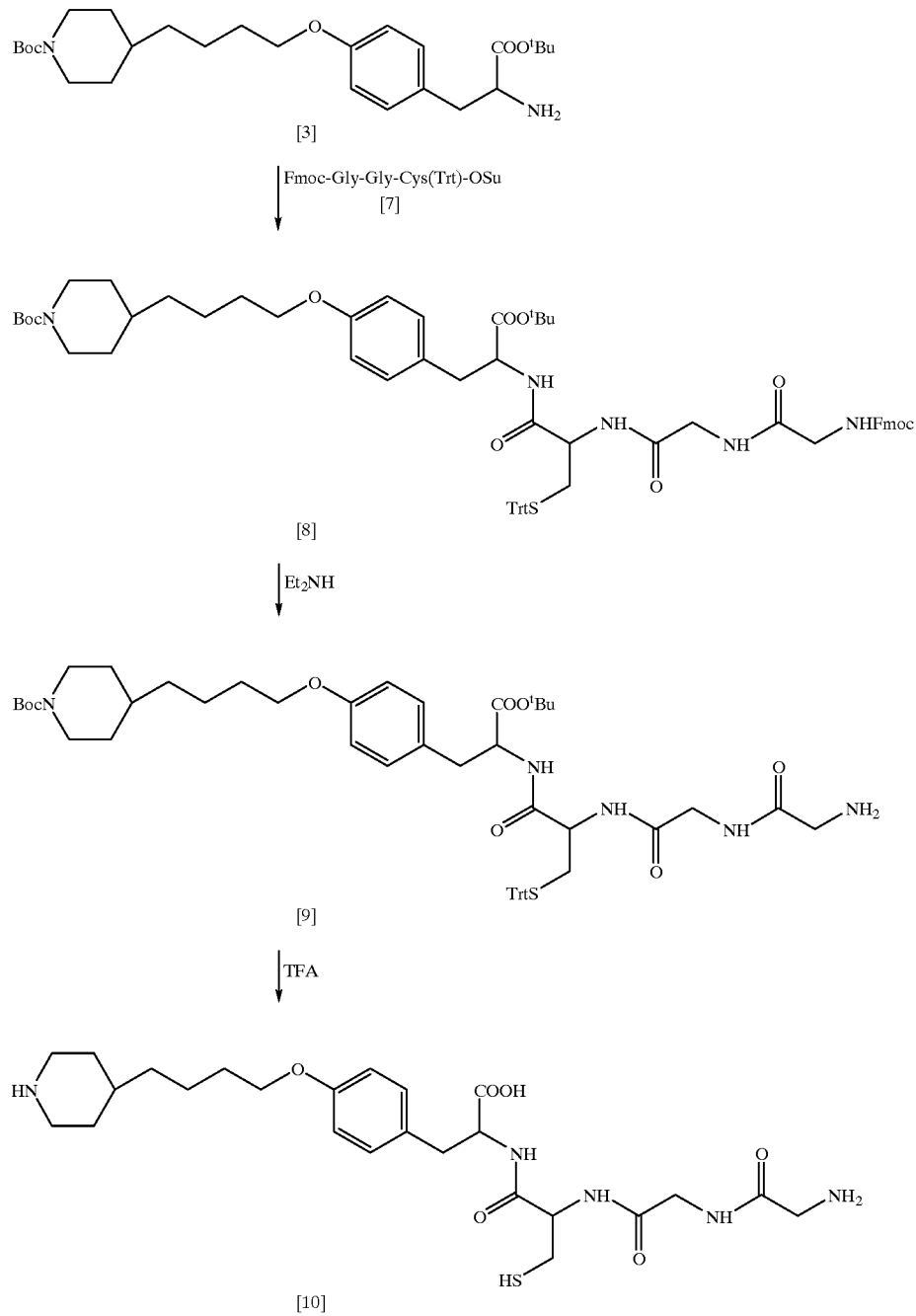

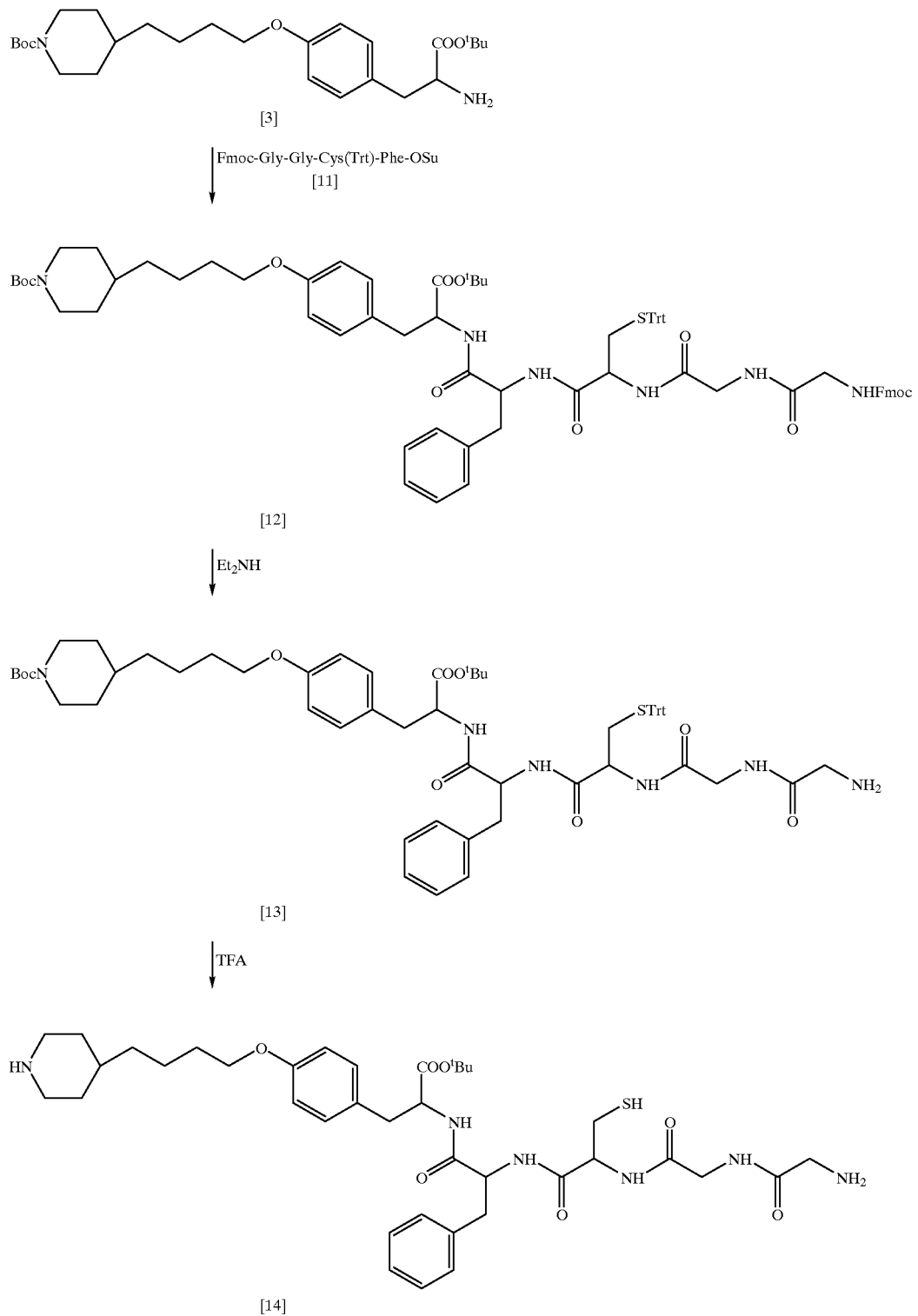

Scheme 4
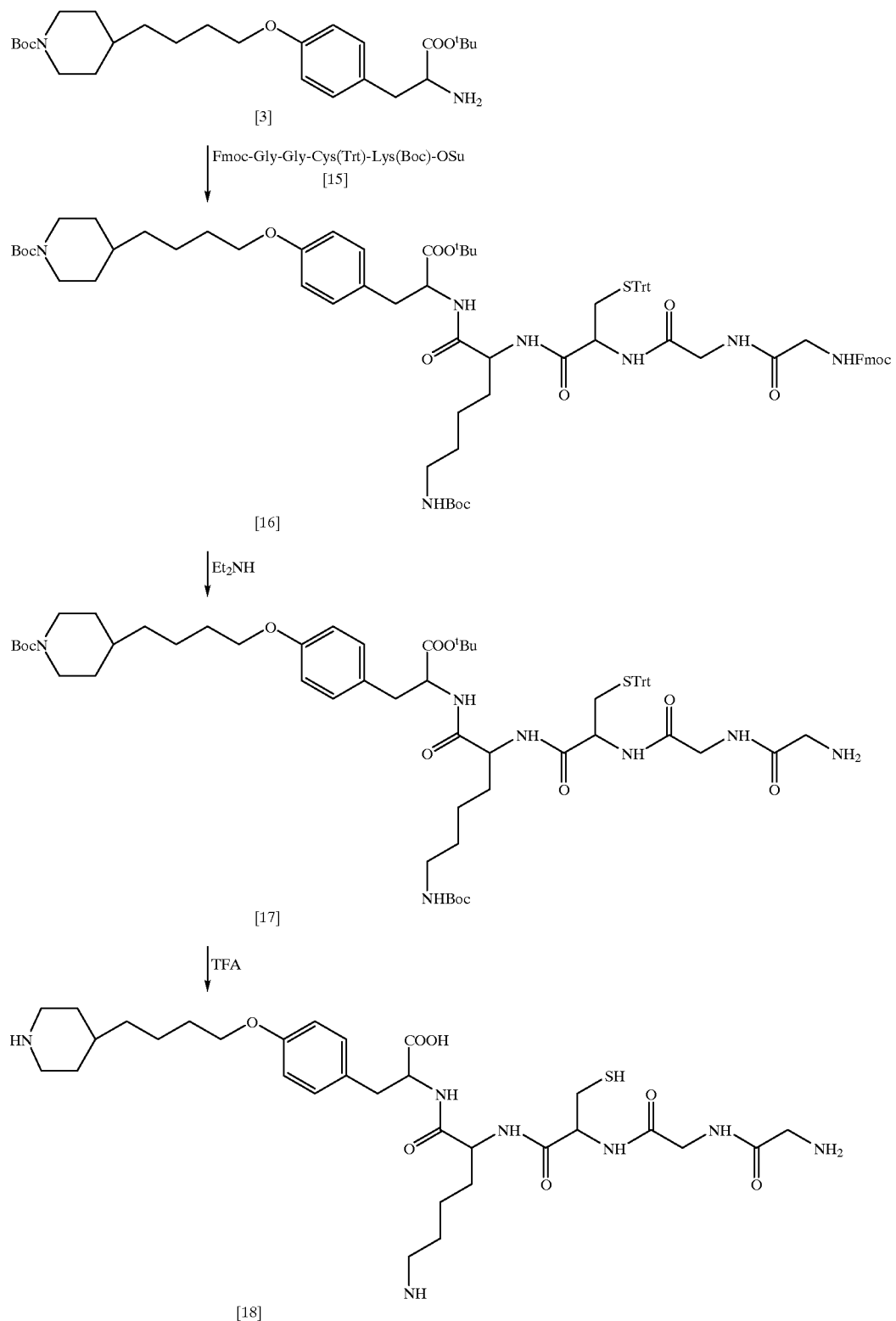

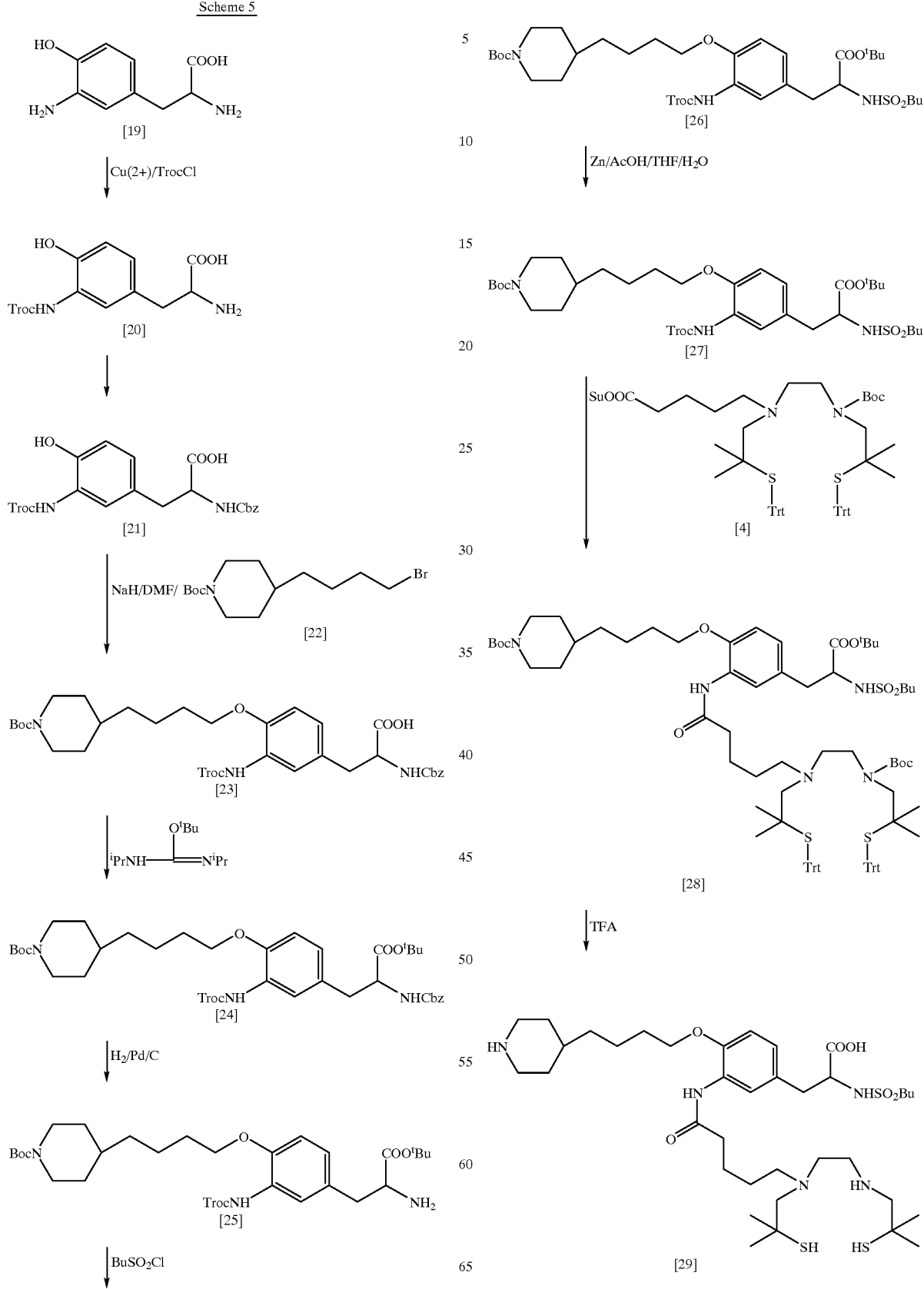

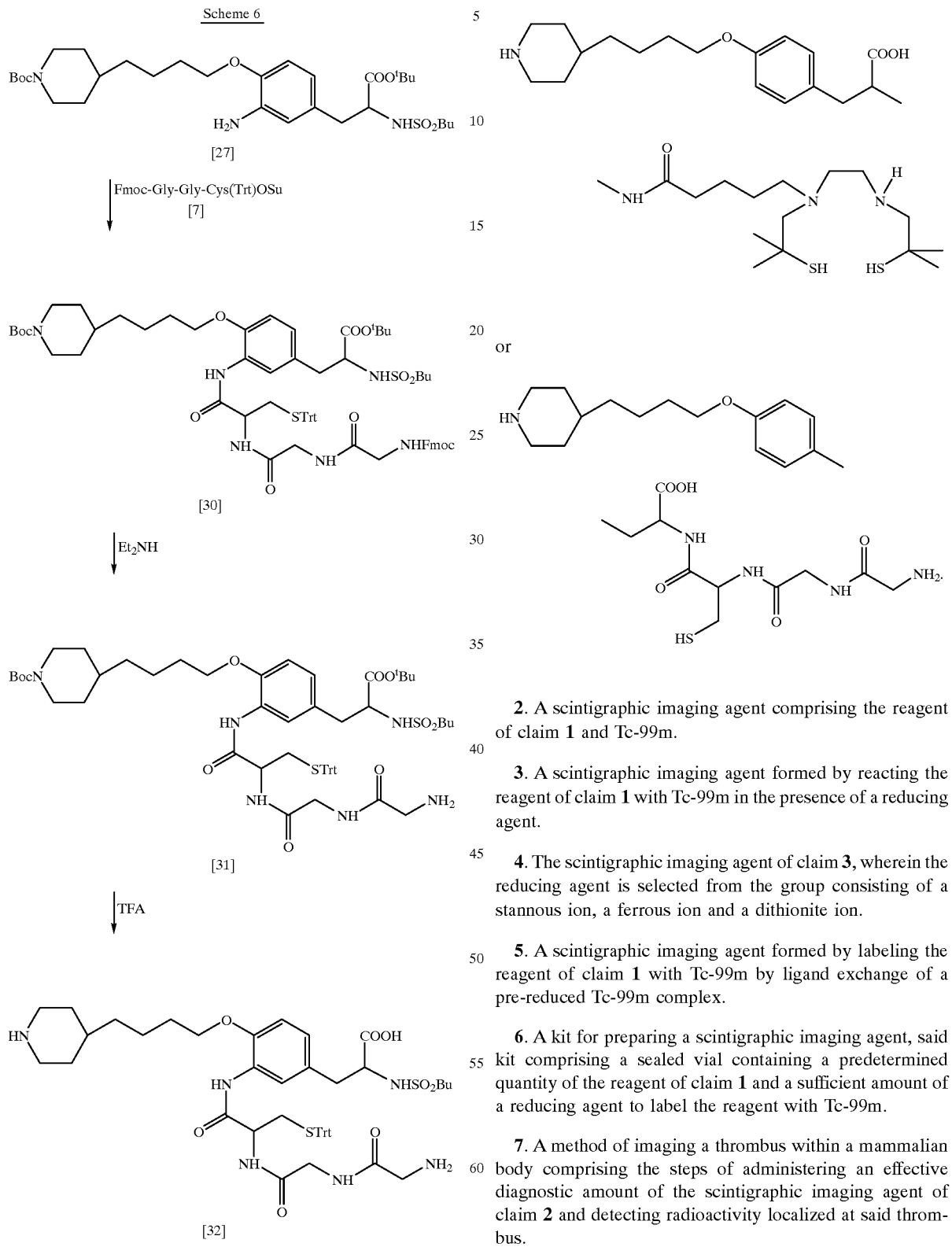

What is claimed is:

1. A reagent having a formula:

[structures shown]

or

[structure shown]

2. A scintigraphic imaging agent comprising the reagent of claim 1 and Tc-99m.

3. A scintigraphic imaging agent formed by reacting the reagent of claim 1 with Tc-99m in the presence of a reducing agent.

4. The scintigraphic imaging agent of claim 3, wherein the reducing agent is selected from the group consisting of a stannous ion, a ferrous ion and a dithionite ion.

5. A scintigraphic imaging agent formed by labeling the reagent of claim 1 with Tc-99m by ligand exchange of a pre-reduced Tc-99m complex.

6. A kit for preparing a scintigraphic imaging agent, said kit comprising a sealed vial containing a predetermined quantity of the reagent of claim 1 and a sufficient amount of a reducing agent to label the reagent with Tc-99m.

7. A method of imaging a thrombus within a mammalian body comprising the steps of administering an effective diagnostic amount of the scintigraphic imaging agent of claim 2 and detecting radioactivity localized at said thrombus.

8. A composition comprising a reagent having a formula:
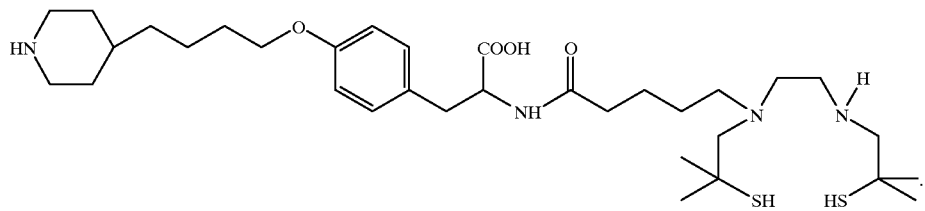
9. A composition comprising a reagent having a formula:
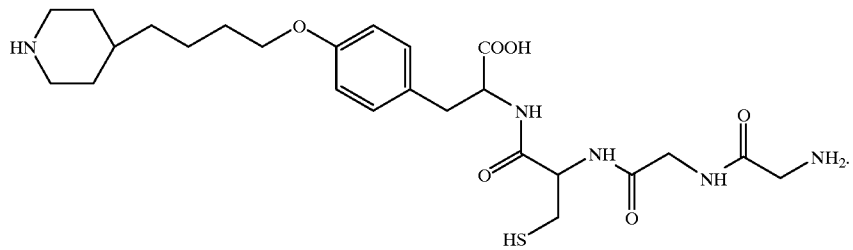
10. A composition comprising a reagent having a formula:
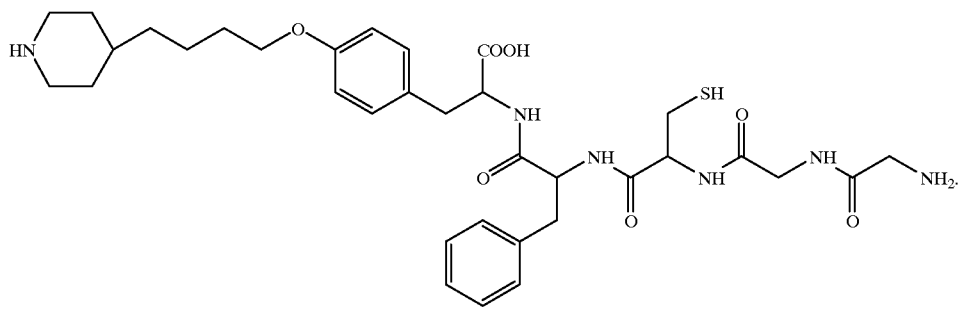
11. A composition comprising a reagent having a formula:
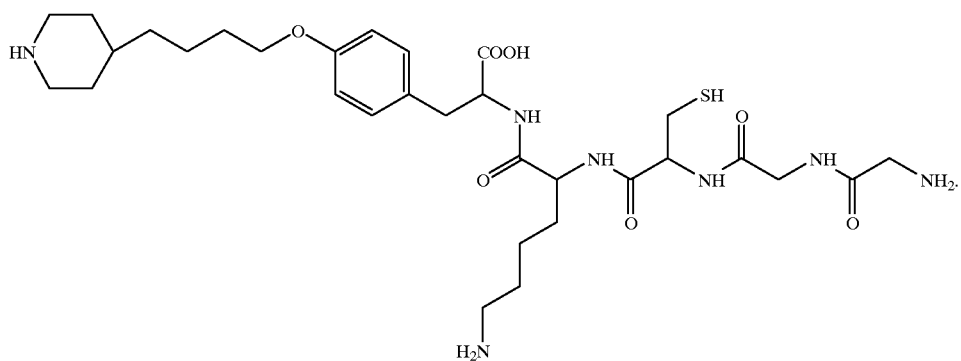

12. A composition comprising a reagent having a formula:
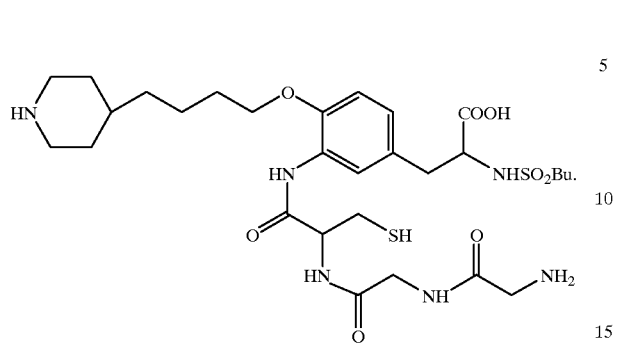
13. A composition comprising a reagent having a formula:
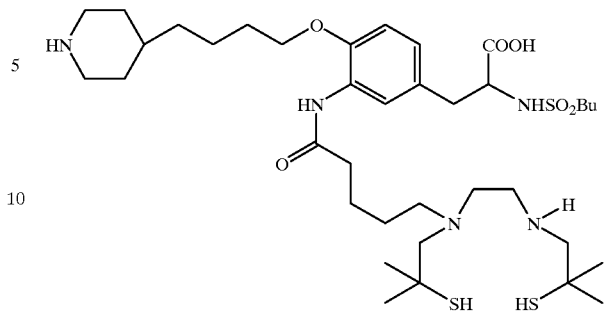
* * * * *